(12) United States Patent (10) Patent No.: US 12,616,401 B2
Oshio et al. (45) Date of Patent: May 5, 2026

(54) PSYCHOLOGICAL STATE DISPLAY SYSTEM

(71) Applicant: Panasonic Intellectual Property Management Co., Ltd., Osaka (JP)

(72) Inventors: Shozo Oshio, Osaka (JP); Mitsuru Nitta, Kyoto (JP); Ryosuke Shigitani, Osaka (JP); Akiko Takimoto, Osaka (JP); Hiroshi Maruyama, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 18/853,448

(22) PCT Filed: Mar. 24, 2023

(86) PCT No.: PCT/JP2023/011737
§ 371 (c)(1),
(2) Date: Oct. 2, 2024

(87) PCT Pub. No.: WO2023/203961
PCT Pub. Date: Oct. 26, 2023

(65) Prior Publication Data
US 2025/0228484 A1 Jul. 17, 2025

(30) Foreign Application Priority Data

Apr. 18, 2022 (JP) ................................. 2022-068534

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/02007* (2013.01); *A61B 5/7264* (2013.01);
(Continued)

(58) Field of Classification Search
CPC .............. A61B 2503/12; A61B 5/0077; A61B 5/02007; A61B 5/165; A61B 5/7264;
(Continued)

(56) References Cited

U.S. PATENT DOCUMENTS

2013/0266925 A1 10/2013 Nunamaker, Jr. et al.
2014/0307926 A1 10/2014 Murakami et al.
(Continued)

FOREIGN PATENT DOCUMENTS

JP 2006-79533 A 3/2006
JP 2009-87303 A 4/2009
(Continued)

OTHER PUBLICATIONS

Extended European Search Report dated Jul. 2, 2025 for corresponding EP Application No. 23791614.3.
International Search Report (ISR) issued on Apr. 25, 2023 in International (PCT) Application No. PCT/JP2023/011737.

*Primary Examiner* — Mark D Remaly
(74) *Attorney, Agent, or Firm* — Renner, Otto, Boisselle & Sklar, LLP

(57) ABSTRACT

A psychological state display system includes a near-infrared light source that outputs outside light toward a plurality of persons, the output light including a first near-infrared radiation having a wavelength of greater than or equal to 780 nm and less than 2,500 nm; an imaging device that receives the first near-infrared radiation included in the output light outputted and captures an infrared image of the plurality of persons; a generation device that, using a trained machine learning model that receives an input of the infrared image captured and outputs a psychological state of at least one person among the plurality of persons indicated by the infrared image, generates psychological data indicating the psychological state; and a display device that displays a change over time in the psychological data generated.

20 Claims, 7 Drawing Sheets

(51) Int. Cl.

| | |
|---|---|
| *A61B 5/02* | (2006.01) |
| *G06V 40/10* | (2022.01) |
| *H04N 23/21* | (2023.01) |
| *H04N 23/74* | (2023.01) |
| *G06V 10/141* | (2022.01) |
| *G06V 10/143* | (2022.01) |

(52) U.S. Cl.
CPC .............. *A61B 5/742* (2013.01); *G06V 40/10* (2022.01); *H04N 23/21* (2023.01); *H04N 23/74* (2023.01); *A61B 2503/12* (2013.01); *G06V 10/141* (2022.01); *G06V 10/143* (2022.01)

(58) Field of Classification Search
CPC .......... A61B 5/742; A61M 2021/0016; A61M 2021/0022; A61M 2021/0027; A61M 2021/0044; A61M 2021/005; A61M 2021/0066; A61M 21/02; A61M 2205/3306; A61M 2205/84; A61M 2210/0606; A61M 2230/06; G06V 10/141; G06V 10/143; G06V 20/52; G06V 40/10; G06V 40/174; G16H 30/40; G16H 50/20; G16H 50/30; G16H 50/70; H04N 23/21; H04N 23/74
See application file for complete search history.

(56) References Cited

U.S. PATENT DOCUMENTS

| | | | |
|---|---|---|---|
| 2017/0102783 A1 | 4/2017 | Shikii et al. | |
| 2017/0181249 A1 | 6/2017 | Takahashi | |
| 2017/0311863 A1 | 11/2017 | Matsunaga | |
| 2019/0139217 A1* | 5/2019 | Szu ...................... | A61B 5/6898 |
| 2019/0300001 A1 | 10/2019 | Watanabe | |
| 2020/0099890 A1 | 3/2020 | Tanaka et al. | |
| 2020/0240658 A1 | 7/2020 | Kitagawa et al. | |

FOREIGN PATENT DOCUMENTS

| | | | |
|---|---|---|---|
| JP | 2014-206903 | A | 10/2014 |
| JP | 2015-169980 | A | 9/2015 |
| JP | 2016-66947 | A | 4/2016 |
| JP | 2016-93313 | A | 5/2016 |
| JP | 2017-073107 | A | 4/2017 |
| JP | 2017-117596 | A | 6/2017 |
| JP | 2018-140162 | A | 9/2018 |
| JP | 6467965 | B2 | 2/2019 |
| JP | 2019-115561 | A | 7/2019 |
| JP | 2020-8278 | A | 1/2020 |
| JP | 2020-48149 | A | 3/2020 |

* cited by examiner

FIG. 5

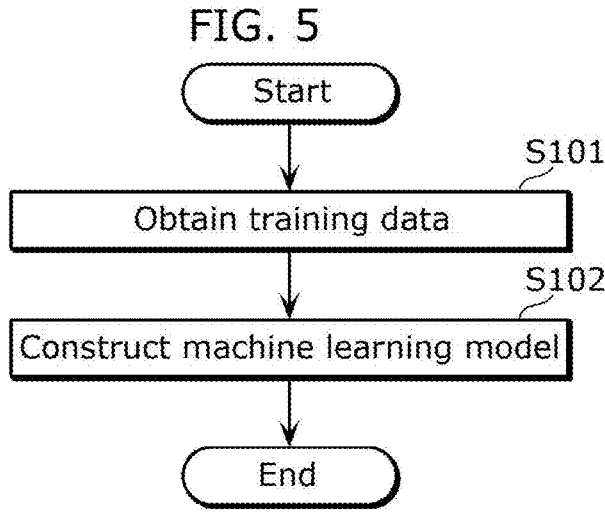

Start

S101
Obtain training data

S102
Construct machine learning model

End

FIG. 6

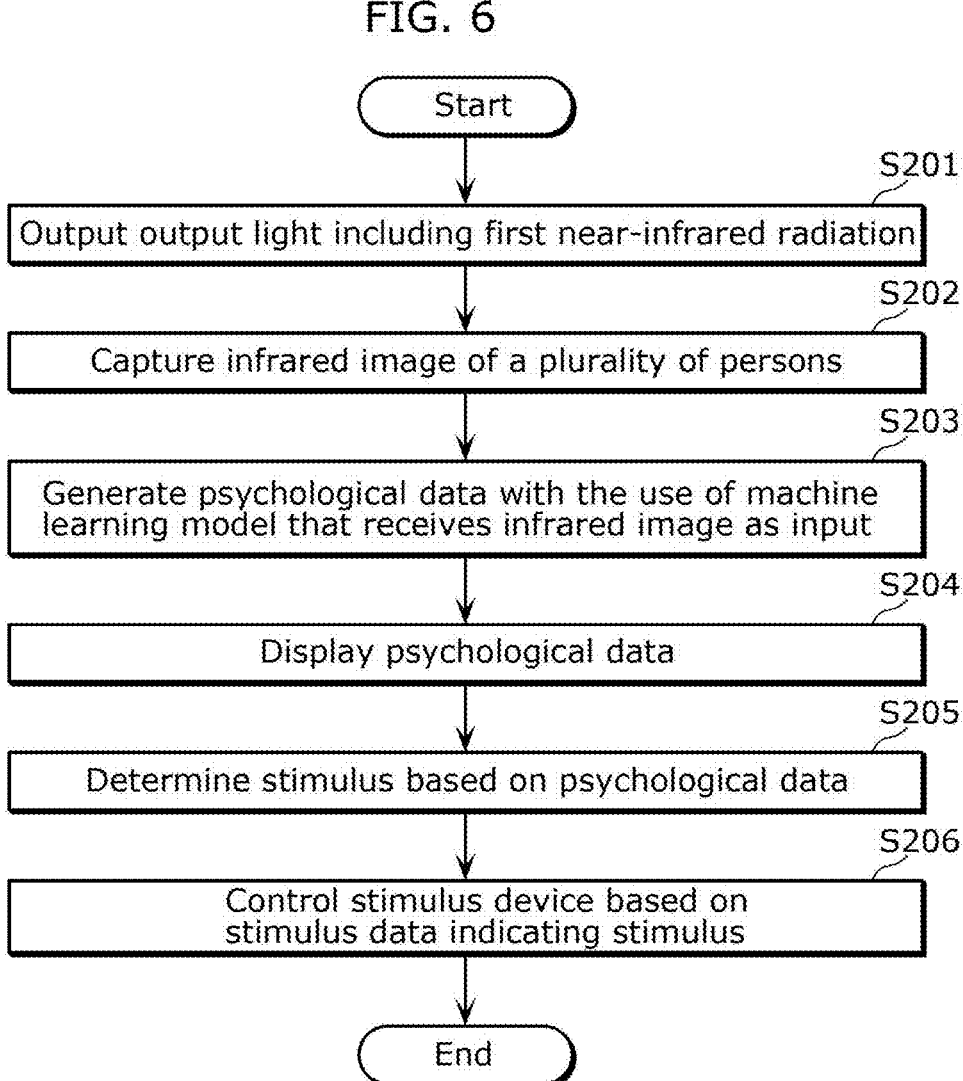

Start

S201
Output output light including first near-infrared radiation

S202
Capture infrared image of a plurality of persons

S203
Generate psychological data with the use of machine learning model that receives infrared image as input S204
Display psychological data S205
Determine stimulus based on psychological data S206
Control stimulus device based on stimulus data indicating stimulus End Level of interest High Low

PSYCHOLOGICAL STATE DISPLAY SYSTEM

TECHNICAL FIELD

The present invention relates to a psychological state display system.

BACKGROUND ART

In recent years, there have been known technologies for estimating a psychological state (an emotion) or the like of a person from an image capturing that person.

For example, Patent Literature (PTL) 1 discloses a system (a facial expression estimating device) that, based on the facial expressions and the movements of a person indicated by an image of that person, estimates a facial expression suitable for that person's psychological state and emotion.

CITATION LIST

Patent Literature

PTL 1
Japanese Unexamined Patent Application Publication No. 2014-206903

SUMMARY OF INVENTION

Technical Problem

Incidentally, the system disclosed in PTL 1 reveals only the temporary psychological state of the person included in the image. It is often the case that the psychological state of a human (a person) changes as the time elapses, and there is a desire to visualize this change.

Accordingly, the present invention is directed to providing a psychological state display system that can visualize a change in the psychological state of a person under the condition where the influence of illumination light is minimized.

Solution to Problem

A psychological state display system according to one aspect of the present invention includes: a near-infrared light source that outputs output light toward a plurality of persons, the output light including a first near-infrared radiation having a wavelength of greater than or equal to 780 nm and less than 2,500 nm; an imaging device that receives the first near-infrared radiation included in the output light outputted and captures an infrared image of the plurality of persons; a generation device that, using a trained machine learning model that receives an input of the infrared image captured and outputs a psychological state of at least one person among the plurality of persons indicated by the infrared image, generates psychological data indicating the psychological state; and a display device that displays a change over time in the psychological data generated.

Advantageous Effects of Invention

The psychological state display system according to the present invention can visualize a change in the psychological state of a person under the condition where the influence of illumination light is minimized.

BRIEF DESCRIPTION OF DRAWINGS

FIG. 5 is a flowchart showing a processing procedure through which a psychological state display system according to an embodiment trains a machine learning model.

FIG. 6 is a flowchart showing a processing procedure through which a psychological state display system according to an embodiment visualizes a psychological state of a person.

DESCRIPTION OF EMBODIMENTS

Figure 1:
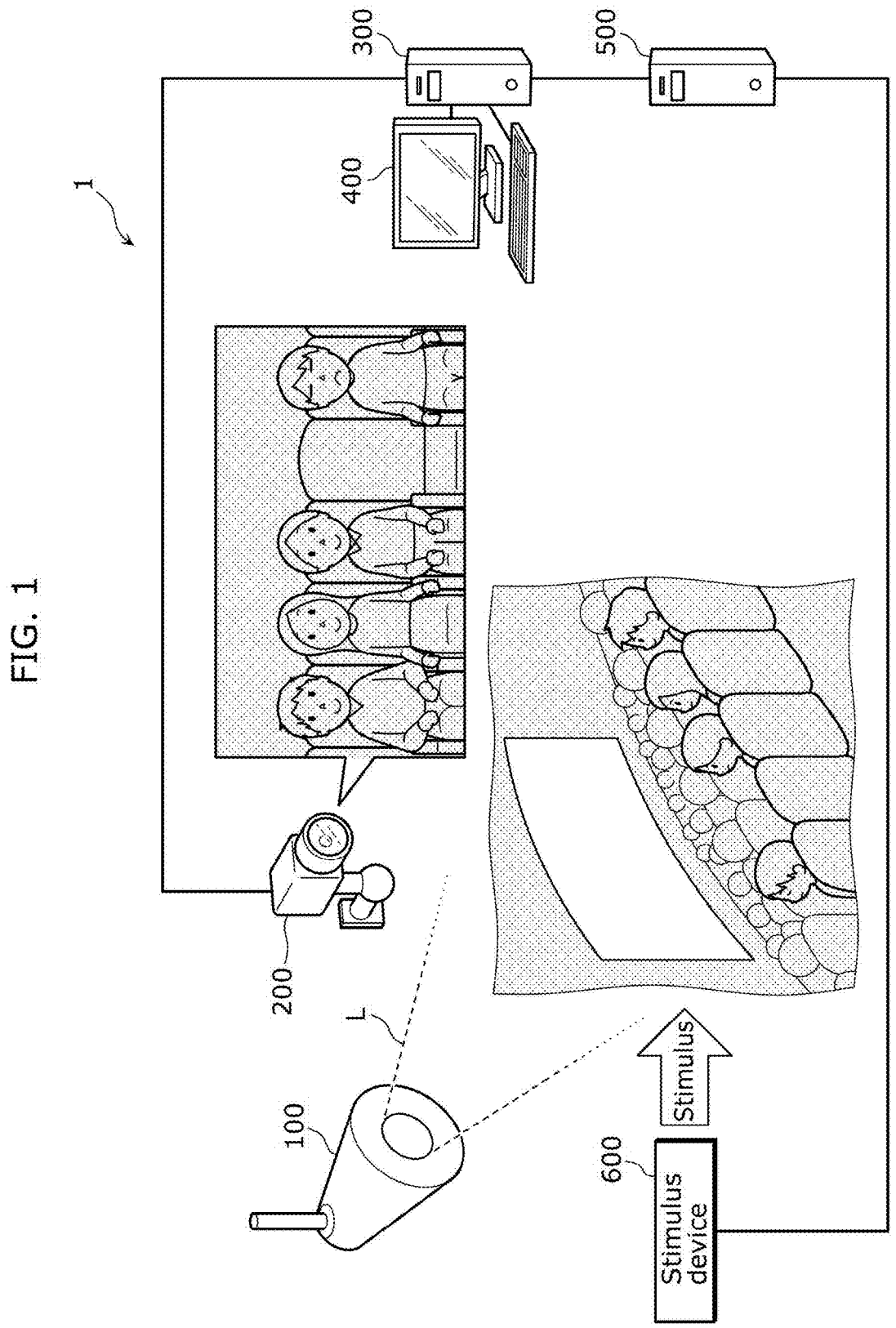
FIG. 1 is a diagram showing a configuration of a psychological state display system according to an embodiment.

Hereinafter, some embodiments will be described in specific terms with reference to the drawings. The embodiments described below merely illustrate general or specific examples. The numerical values, the shapes, the materials, the constituent elements, the arrangement positions and the connection modes of the constituent elements, the steps, the orders of the steps, and so on illustrated in the following embodiment are examples and are not intended to limit the present invention. Among the constituent elements described in the following embodiments, any constituent elements that are not cited in the independent claims are to be construed as optional constituent elements.

The drawings are schematic diagrams and do not necessarily provide the exact depiction. In the drawings, substantially identical configurations are given identical reference characters, and duplicate description thereof may be omitted or simplified.

Embodiment

Configuration of Psychological State Display System

A configuration of psychological state display system 1 according to the present embodiment will be described.

Figure 2:
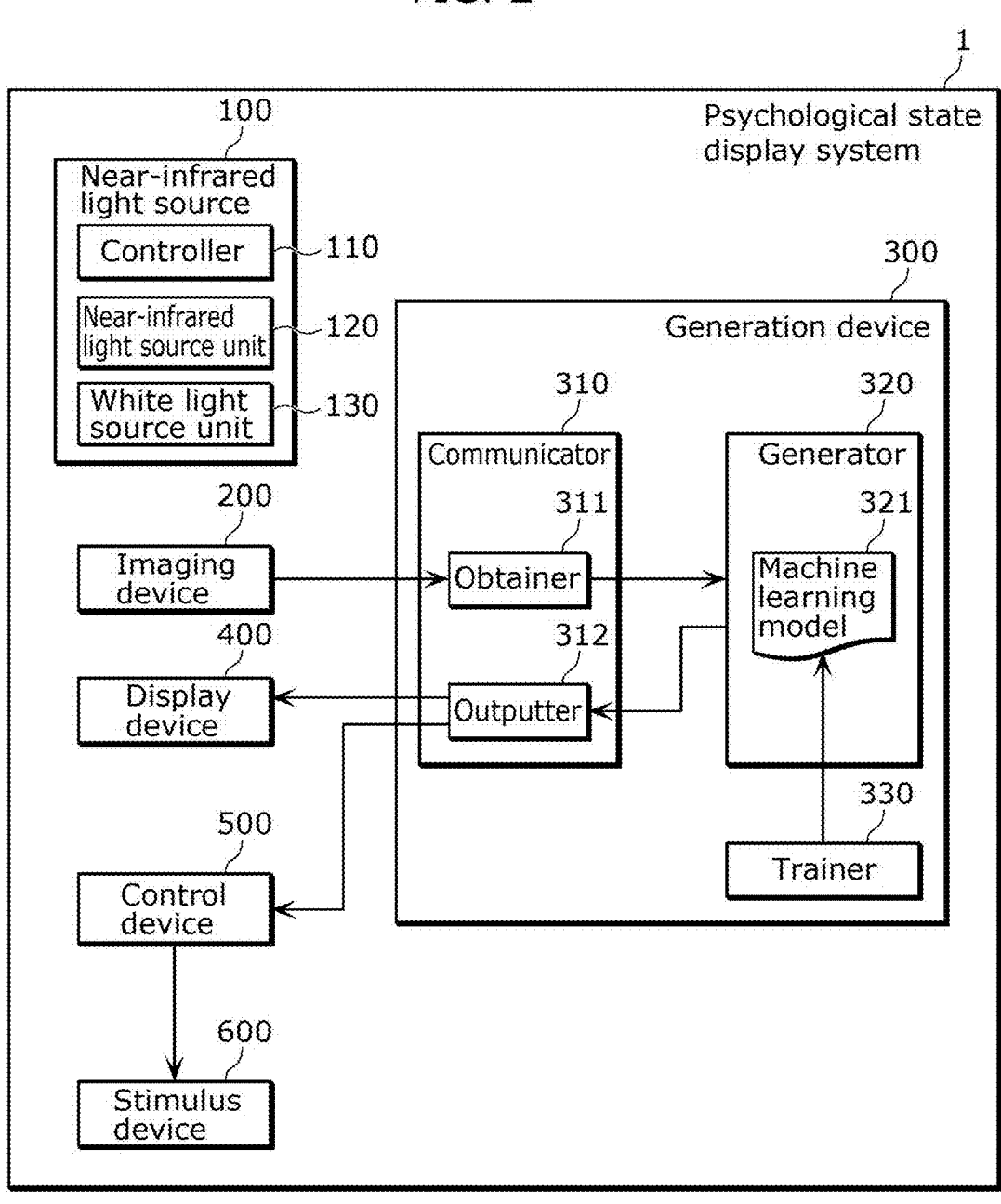
FIG. 2 is a block diagram showing a characteristic functional configuration of a psychological state display system according to an embodiment.

FIG. 1 is a diagram showing a configuration of psychological state display system 1 according to the present embodiment. FIG. 2 is a block diagram showing a characteristic functional configuration of psychological state display system 1 according to the present embodiment.

Psychological state display system 1 outputs output light L including a near-infrared radiation toward a plurality of persons (e.g., no less than a few persons and no more than a few dozens of persons), and captures an infrared image of this plurality of persons. Based on the infrared image captured, psychological state display system 1 generates psychological data indicating a psychological state of at least one person among the plurality of persons, and displays a change over time in this psychological data. When, for example, an administrator or the like of psychological state display system 1 looks at the displayed change over time in the psychological data, the administrator or the like can understand the change in the psychological state of the plurality of persons and so on. In other words, psychological state display system 1 can visualize a change in the psychological state of a person.

Furthermore, psychological state display system 1 determines a stimulus based on the psychological data, and provides the determined stimulus to the plurality of persons. Accordingly, psychological state display system 1 can provide a person with a stimulus that changes the psychological state of that person, in accordance with the psychological state of that person, and thus psychological state display system 1 can control the psychological state of that person.

Examples of the psychological state according to the present embodiment include being happy, being sad, feeling energetic, being scared, being angry, feeling depressed, being alert, being absent-minded, being interested, feeling nervous, and being concentrated, but these are not limiting examples.

As shown in FIG. 1 and FIG. 2, psychological state display system 1 includes near-infrared light source 100, imaging device 200, generation device 300, display device 400, control device 500, and stimulus device 600.

Near-infrared light source 100 outputs, toward a plurality of persons, output light L including a first near-infrared radiation having a wavelength of greater than or equal to 780 nm and less than 2,500 nm. With the use of such near-infrared light source 100, a large space is irradiated with the first near-infrared radiation.

Imaging device 200 receives the first near-infrared radiation included in outputted output light L, and captures an infrared image of the plurality of persons. Imaging device 200 captures the infrared image of the plurality of persons by receiving the first near-infrared radiation reflected by the plurality of persons.

With the use of trained machine learning model 321 that, in response to receiving the captured infrared image as an input, outputs the psychological state of at least one person among the plurality of persons included in the infrared image, generation device 300 generates psychological data indicating that psychological state. Furthermore, based on the generated psychological data, generation device 300 determines a stimulus to be provided to the plurality of persons. Herein, generation device 300 can be implemented, for example, with the use of the techniques and so on described in Japanese Patent No. 6467965.

Display device 400 displays a change over time in the generated psychological data.

Control device 500 controls stimulus device 600 so that the determined stimulus is provided to the plurality of persons.

Stimulus device 600 provides the stimulus to the plurality of persons.

In one example, psychological state display system 1 according to the present embodiment is a system that is used in a space such as an entertainment space, a public space, or a learning space, but spaces where psychological state display system 1 according to the present embodiment can be used are not limited to the examples above. At least near-infrared light source 100, imaging device 200, and stimulus device 600 are installed in a space like the ones mentioned above. Generation device 300, display device 400, and control device 500 may also be installed in that space or may be installed at a remote location away from that space.

In FIG. 1, in a movie theater serving as one example of an entertainment space, output light L is outputted toward a plurality of persons watching the movie, an infrared image of this plurality of persons is captured, and a change over time in the psychological states of this plurality of persons are visualized. Furthermore, a stimulus is provided to this plurality of persons.

Now, constituent elements included in psychological state display system 1 will be described.

Near-infrared light source 100 is a light source that outputs output light L including a first near-infrared radiation toward a plurality of persons. The first near-infrared radiation is light having a wavelength of greater than or equal to 780 nm and less than 2,500 nm. Herein, while the first near-infrared radiation may include the entire wavelengths in the range of wavelengths greater than or equal to 780 nm and less than 2,500 nm, it suffices that the first near-infrared radiation include wavelengths in at least a part of the stated range. Furthermore, the first near-infrared radiation has a peak wavelength in the range of wavelengths greater than or equal to 780 nm and less than 2,500 nm.

Herein, it is preferable that the first near-infrared radiation be light that has a wavelength of (i) greater than or equal to 780 nm and less than 1,700 nm, or it is more preferable that the first near-infrared radiation be light that has a wavelength of (ii) greater than or equal to 780 nm and less than 1,500 nm. It is further preferable that the first near-infrared radiation be light that has a wavelength of (iii) greater than or equal to 780 nm and less than 900 nm, or it is even more preferable that the first near-infrared radiation be light that has a wavelength of (iv) greater than or equal to 800 nm and less than 900 nm. Herein, the first near-infrared radiation may have a peak wavelength in the range of any of the wavelengths stated in (i), (ii), (iii), or (iv) above.

According to the present embodiment, near-infrared light source 100 outputs output light L that includes the first near-infrared radiation described above and visible light. The visible light is light having a wavelength of greater than or equal to 380 nm and less than 780 nm. The visible light may be monochromatic light, such as red light, green light, or blue light. In this example, the visible light is white light.

Near-infrared light source 100 controls the first near-infrared radiation and the visible light independently of each other, and thus controls at least one of the on/off or the dimming of each of the first near-infrared radiation and the visible light. To be more specific, controller 110 of near-infrared light source 100 controls the first near-infrared radiation and the visible light independently of each other, and thus controls at least one of the on/off or the dimming of each of the first near-infrared radiation and the visible light. For example, near-infrared light source 100 can control at least one of the on/off or the dimming of the first near-infrared radiation alone while maintaining the emission mode of the visible light constant. In a similar manner, near-infrared light source 100 can control at least one of the on/off or the dimming of the visible light alone while maintaining the emission mode of the first near-infrared radiation constant.

Near-infrared light source 100 according to the present embodiment includes near-infrared light source unit 120 that emits the first near-infrared radiation and white light source unit 130 that emits the visible light (the white light). Controller 110 performs controls so as to cause near-infrared light source unit 120 to emit the first near-infrared radiation and so as to cause white light source unit 130 to emit the visible light (the white light).

In one example, near-infrared light source unit 120 includes a first solid-state light emitting element. The first solid-state light emitting element may be, for example but is not limited to, a laser diode element. In this example, the first solid-state light emitting element is a near-infrared LED element. The near-infrared LED element converts given electric power to light (the first near-infrared radiation) and emits the converted light.

In another example, near-infrared light source unit 120 includes a second solid-state light emitting element and a phosphor member. The second solid-state light emitting element is an element that outputs excitation light and may be, for example but is not limited to, a laser diode element. In this example, the second solid-state light emitting element is a blue LED element. In other words, the second solid-state light emitting element outputs blue light as the excitation light. The phosphor member is a member that outputs wavelength-converted light, or the first near-infrared radiation, based on the received excitation light (the blue light). Examples of the phosphor member include a $Cr^{3+}$ activated phosphor, which is easy to manufacture, or a rare-earth activated phosphor (in particular, a phosphor activated by at least one selected from $Tm^{3+}$, $Er^{3+}$, $Nd^{3+}$, and $Yb^{3+}$).

Now, a case in which near-infrared light source unit 120 that includes the second solid-state light emitting element and the phosphor member is used will be further described. As stated above, the first near-infrared radiation is light having a wavelength of greater than or equal to 780 nm and less than 2,500 nm. When the first near-infrared radiation is light having a wavelength in any of (i), (ii), (iii), and (iv) above, commercially available near-infrared light source unit 120 can be used. As to commercially available near-infrared light source unit 120, a near-infrared light source unit having a fluorescence peak at a wavelength selected from 780 nm, 850 nm, 940 nm, 980 nm, 1,050 nm, 1,200 nm, 1,300 nm, 1,400 nm, 1,450 nm, 1,500 nm, 1,550 nm, 1,600 nm, and 1,650 nm is used. As to the $Cr^{3+}$ activated phosphor described above, a $Cr^{3+}$ activated phosphor having a fluorescence peak at a wavelength selected, for example, from 790 nm, 800 nm, 825 nm, 850 nm, 880 nm, 925 nm, 950 nm, 970 nm, and 1,035 nm is used. As to the rare-earth activated phosphor, the following applies. For example, a $Tm^{3+}$ activated phosphor has a property where the $Tm^{3+}$ activated phosphor has an emission line-type fluorescence peak wavelength at roughly 785 nm, 800 nm, or 820 nm. For example, an $Er^{3+}$ activated phosphor has a property where the $Er^{3+}$ activated phosphor has an emission line-type fluorescence peak wavelength at roughly 970 nm, 1,005 nm, 1,470 nm, 1,530 nm, 1,570 nm, 1,615 nm, or 1,645 nm. For example, a $Nd^{3+}$ activated phosphor has a property where the $Nd^{3+}$ activated phosphor has an emission line-type fluorescence peak wavelength at 880 nm, 935 nm, 1,060 nm, 1,105 nm, 1,335 nm, or 1,420 nm. For example, a $Yb^{3+}$ activated phosphor has a property where the $Yb^{3+}$ activated phosphor has an emission line-type fluorescence peak wavelength at 970 nm, 1,000 nm, or 1,025 nm.

White light source unit 130, which emits the visible light (the white light) includes, for example, a yellow phosphor member and a blue LED element. A part of the blue light serving as the excitation light outputted from the blue LED element gets its wavelength converted by the yellow phosphor member and turns into yellow light. As this yellow light and the part of the blue light that does not get its wavelength converted are combined, white light is outputted from white light source unit 130. Herein, the configuration of white light source unit 130 is not limited to the one described above as long as white light source unit 130 can output visible light, such as the white light.

In this manner, near-infrared light source 100 outputs, toward a plurality of persons, output light L that includes the first near-infrared radiation emitted by near-infrared light source unit 120 and the visible light (the white light) emitted by white light source unit 130. According to the present embodiment, output light L is kept on, that is, is outputted continuously while psychological state display system 1 generates psychological data and a change over time in this psychological data is displayed.

With this configuration, imaging device 200 can capture an image of the plurality of persons continuously, and generation device 300 can generate psychological data continuously. Therefore, display device 400 can continuously display the generated psychological data and can thus display a change over time in the psychological data.

Meanwhile, the output of the first near-infrared radiation that near-infrared light source 100 (near-infrared light source unit 120 to be more specific) emits is greater than or equal to 10 W and smaller than or equal to 3 kW. For example, the output of the first near-infrared radiation may be an output of 30 W, 100 W, 300 W, 1 KW, or 3 KW. Herein, in order to cause near-infrared light source 100 to output a first near-infrared radiation of a higher output, near-infrared light source 100 may include a plurality of near-infrared light source units 120. Furthermore, according to the present embodiment, psychological state display system 1 includes one near-infrared light source 100. This, however, is not a limiting example, and psychological state display system 1 may include a plurality of near-infrared light sources 100.

With this configuration, near-infrared light sources 100 can emit the first near-infrared radiation that reaches a plurality of persons located in a region away from near-infrared light sources 100. In other words, the configuration above can realize psychological state display system 1 that can visualize a change in the psychological state of a plurality of persons located in a region away from near-infrared light sources 100.

Imaging device 200 is a device that receives the first near-infrared radiation including output light L outputted by near-infrared light source 100 and captures an infrared image of a plurality of persons. One example of imaging device 200 is an infrared camera. Herein, imaging device 200 may continuously capture an infrared image while near-infrared light source 100 outputs the first near-infrared radiation.

Upon output light L (the first near-infrared radiation) being outputted toward a plurality of persons, the first near-infrared radiation is reflected by this plurality of persons. Imaging device 200 receives the first near-infrared radiation reflected by the plurality of persons and thus captures an infrared image of the plurality of persons. This infrared image is a still image and captures the plurality of persons. According to the present embodiment, an infrared image captures at least one of the face or the body of each of a plurality of persons.

Imaging device 200 captures an infrared image at predetermined time intervals. In other words, imaging device 200 captures one infrared image and, after a predetermined time has passed, captures another infrared image, and imaging device 200 repeats this process. The predetermined time is, for example, a few seconds or more and a few minutes or less, but this is not a limiting example. In one example, imaging device 200 captures an infrared image (a still image) every five seconds. Herein, imaging device 200 may capture an infrared moving image, instead of an infrared image (a still image). In this case, each of the frame images of the infrared moving image may be used as an infrared image.

Imaging device 200 outputs each captured infrared image to generation device 300. As described above, imaging device 200 repeatedly captures an infrared image. For example, imaging device 200, upon capturing one infrared image and outputting that infrared image to generation device 300, captures another infrared image and outputs that infrared image to generation device 300. In other words, imaging device 200 repeats the process of outputting one infrared image to generation device 300 each time imaging device 200 captures an infrared image. Alternatively, for example, imaging device 200 may first capture a plurality of infrared images and then output the plurality of infrared images at once to generation device 300.

According to the present embodiment, each captured infrared image is outputted to generation device 300 by a communicator included in imaging device 200. This communicator is a communication circuit for imaging device 200 to communicate with generation device 300. According to the present embodiment, the stated communicator is a circuit for wireless communication and performs wireless communication, specifically, in accordance with the communication standards such as Bluetooth (registered trademark) Low Energy (BLE) or Wi-Fi (registered trademark). Herein, the communicator may be a circuit for wired communication.

Now, the received light signal intensity of imaging device 200 will be described.

As described above, imaging device 200 receives the first near-infrared radiation reflected by a plurality of persons while output light L including the first near-infrared radiation is being outputted. The received light signal intensity obtained as this first near-infrared radiation is received is referred to as a first received light signal intensity. The first received light signal intensity is the intensity of the received light signal corresponding to the electric charge generated as imaging device 200 (an image sensor included in imaging device 200 to be more specific) receives the first near-infrared radiation.

Meanwhile, there may be a case in which a second near-infrared radiation different from the first near-infrared radiation is emitted toward a plurality of persons. The second near-infrared radiation is a near-infrared radiation outputted from a light source different from near-infrared light source 100. The second near-infrared radiation is, for example, a near-infrared radiation included in the sunlight. This, however, is not a limiting example, and the second near-infrared radiation may also be a near-infrared radiation outputted from an illumination device. In the case described below, the second near-infrared radiation is emitted toward a plurality of persons while output light L including the first near-infrared radiation is not being outputted. Imaging device 200 receives the second near-infrared radiation reflected by the plurality of persons. The received light signal intensity obtained as this second near-infrared radiation is received is referred to as a second received light signal intensity. The second received light signal intensity is the intensity of the received light signal corresponding to the electric charge generated as imaging device 200 (an image sensor included in imaging device 200 to be more specific) receives the second near-infrared radiation.

According to the present embodiment, the minimum value of the first received light signal intensity is greater than the maximum value of the second received light signal intensity. For example, the minimum value of the first received light signal intensity is preferably two times or more the maximum value of the second received light signal intensity, more preferably five times or more the maximum value of the second received light signal intensity, or even more preferably ten times or more the maximum value of the second received light signal intensity.

Herein, when the output of the first near-infrared radiation is set to an output of greater than or equal to 10 W and smaller than or equal to 3 kW, that is, when the output of the first near-infrared radiation is set sufficiently high, the minimum value of the first near-infrared radiation can be made greater than the maximum value of the second received light signal intensity.

With this configuration, the intensity of the second received light signal, which can result in noise in the signal for recognizing a plurality of persons, can be kept sufficiently small. As such noise can be kept sufficiently small, an infrared image capturing a plurality of persons with higher accuracy can be captured with imaging device 200.

Imaging device 200 may include a magnification controlling mechanism (not shown) that controls the magnification of an infrared image to be captured. This configuration is advantageous in obtaining an infrared image in which a lens or the like included in the magnification controlling mechanism has put a focus on each of the plurality of persons.

Generation device 300 is a device that generates psychological data indicating a psychological state with the use of a captured infrared image and trained machine learning model 321. Based on the generated psychological data, generation device 300 determines a stimulus to be provided to a plurality of persons. Generation device 300 is, for example, a personal computer. Alternatively, generation device 300 may be a server device with a high computational capability that is connected to a network.

In this example, generation device 300 includes communicator 310, generator 320, and trainer 330.

Communicator 310 is a communication circuit for generation device 300 to communicate with imaging device 200, display device 400, and control device 500. According to the present embodiment, communicator 310 is a circuit for wireless communication and performs wireless communication, specifically, in accordance with the communication standards such as BLE or Wi-Fi (registered trademark). Herein, communicator 310 may be a circuit for wired communication.

Communicator 310 includes obtainer 311 and outputter 312. Obtainer 311 obtains an infrared image captured and outputted by imaging device 200. As described above, imaging device 200 repeats the process of capturing an infrared image and the process of outputting that infrared image. Therefore, obtainer 311 successively obtains an outputted infrared image. To rephrase, obtainer 311 obtains an outputted plurality of infrared images. Meanwhile, outputter 312 outputs generated psychological data to display device 400 and outputs stimulus data indicating a determined stimulus to control device 500.

Generator 320 generates psychological data based on an infrared image obtained by obtainer 311. To be more specific, generator 320 includes machine learning model 321, and with the use of this machine learning model 321, generates psychological data indicating the psychological state of at least one person among the plurality of persons. Each time generator 320 obtains one infrared image, generator 320 generates one item of psychological data corresponding to the obtained one infrared image.

As stated above, examples of the psychological state include being happy, being sad, feeling energetic, being scared, being angry, feeling depressed, being alert, being absent-minded, being interested, and feeling nervous, but these are not limiting examples.

Machine learning model 321 is a trained model that, in response to receiving an infrared image obtained by obtainer 311 as an input, outputs the psychological state of at least one person among the plurality of persons captured in the infrared image. According to the present embodiment, trainer 330 trains machine learning model 321.

Psychological data, for example, is data that indicates the psychological state of at least one person among a plurality of persons, is data that display device 400 displays, and is, more specifically, digital data. Examples of the psychological data include displaying data such as numerical value displaying data, color displaying data, pattern displaying data, graphical symbol displaying data, emoji displaying data, and illustration displaying data. Furthermore, according to the present embodiment, psychological data is image data in which at least one of the items of data listed above is superposed on a captured infrared image. When the psychological data is image data, the image data is displayed on display device 400 with the plurality of persons captured in the infrared image and the corresponding psychological states of these persons mapped to each other.

Based on the generated psychological data, generator 320 determines a stimulus to be provided to the plurality of persons. For example, generator 320 determines a stimulus to be provided to the plurality of persons based on the generated psychological data and correspondence data stored in a storage (not shown) included in generation device 300. The correspondence data is data that indicates the psychological states indicated by the psychological data and stimuli corresponding to these psychological states. By referring to the correspondence data, generator 320 determines, as the stimulus to be provided to the plurality of persons, the stimulus corresponding to the generated psychological data. Herein, providing a stimulus to a person is expected to change the psychological state of that person. The stimulus data indicates the stimulus determined in this manner. With this configuration, a stimulus for changing a person's psychological state can be determined in accordance with the psychological state of that person.

Generator 320 configured as described above is implemented, specifically, by a processor, a microcomputer, or a dedicated circuit that executes a program.

Trainer 330 trains machine learning model 321 with the use of training data. Trainer 330 is implemented, specifically, by a processor, a microcomputer, or a dedicated circuit that executes a program.

Trainer 330 trains and constructs machine learning model 321. Trainer 330 provides constructed machine learning model 321 to generator 320. Herein, trainer 330 is not an essential constituent element and does not have to be provided in psychological state display system 1.

This machine learning model 321 is a model for generating psychological data.

According to the present embodiment, machine learning model 321 is a model constructed through machine learning where one or more data sets are used as training data. One data set is composed of a set of an infrared image captured by imaging device 200 and the psychological state of the person captured in the infrared image. Herein, this infrared image captures at least one of the face or the body of that person. The infrared image preferably captures the entire face or the entire body of that person, but this is not a limiting example. For example, it suffices that the infrared image capture a part of the face of that person or a part of the body of that person.

To rephrase, machine learning model 321 is a recognition model constructed through machine learning where one or more data sets each composed of an infrared image and the psychological state of the person captured in that infrared image are used as training data. To be more specific, machine learning model 321 is a recognition model constructed so as to, in response to receiving as input data of an infrared image belonging to each of the one or more data sets serving as the training data, output as output data the psychological state of the person captured in the infrared image belonging to the data set.

In one example, trainer 330 trains the model with the use of machine learning, as described above. Therefore, according to the present embodiment, the model is machine learning model 321.

Herein, trainer 330 may train machine learning model 321 with the use of, for example, a neural network, or more specifically, with the use of a convolutional neural network (CNN). When machine learning model 321 is a convolutional neural network, trainer 330 determines, for example, the coefficient (the weight) of the filter of a convolution layer through machine learning that is based on training data.

Alternatively, trainer 330 may train machine learning model 321 with the use of an algorithm other than that for a neural network.

Display device 400 displays a change over time in the psychological data outputted from generation device 300. To be more specific, since, each time generator 320 obtains one infrared image, generator 320 generates and outputs one item of psychological data corresponding to the obtained one infrared image, display device 400 successively obtains and displays the outputted psychological data. Thus, display device 400 displays a change over time in the psychological data.

Display device 400 is a monitor device of an emission type or a non-emission type. Display device 400 is constituted, for example, by an organic electroluminescence (EL) panel, which is a monitor device of an emission type, or by a liquid crystal panel, which is a monitor device of a non-emission type. Display device 400 may be of a desktop type or of a portable type. Examples of display device 400 of a desktop type include a display for a monitor of a personal computer, and examples of display device 400 of a portable type include a smartphone or a tablet terminal.

Display device 400 is, for example, a device that can be viewed by an administrator or the like of psychological state display system 1. As such an administrator looks at a displayed change over time in the psychological state, the administrator can understand a change over time in the psychological state of the plurality of persons. In other words, psychological state display system 1 can visualize a change in the psychological state of a person.

As a change in the psychological state of a person is visualized in this manner, the administrator looking at display device 400 can gain the following knowledge, for example.

When psychological state display system 1 is used in a space with a plurality of persons, the administrator can promptly find, from among the plurality of persons, a nervous suspicious person or a person feeling depressed as he or she, being overwhelmed by a large crowd, cannot speak out.

Furthermore, when psychological state display system 1 is used in a seminar room (one example of a learning space)

where a seminar is held, psychological state display system 1 can reveal the psychological states, such as the levels of interest, of the seminar participants. In this case, the administrator may be able to let the speaker know of the timing to take a break.

Control device 500 is a device that controls stimulus device 600 and is, for example, a personal computer. Alternatively, control device 500 may be a server device with a high computational capability that is connected to a network. Herein, control device 500 may be any other devices that can control stimulus device 600 and may, for example, be a device dedicated to control stimulus device 600.

Control device 500 obtains stimulus data outputted from generation device 300. Control device 500 controls stimulus device 600 so that stimulus device 600 can provide a stimulus indicated by the obtained stimulus data to a plurality of persons.

This configuration makes it possible to provide, to a person, a stimulus for changing the psychological state of that person in accordance with that person's psychological state, and thus makes it possible to implement psychological state display system 1 that can control the psychological state of that person.

Stimulus device 600 is a device that is controlled by control device 500 and provides a stimulus to a plurality of persons. This stimulus is a stimulus that acts on at least one of the vision, the hearing, the smell, or the touch of a plurality of persons. The stimulus is at least one stimulus selected, for example, from light, a sound, a smell, a vibration, a wind, a temperature, and a humidity. When the stimulus is light, this includes a case in which the stimulus is a video image. In one example, stimulus device 600 is a light source device, a projector device, a loudspeaker, a vibration device, a wind blowing device, a temperature adjusting device, or a humidity adjusting device, but these are not limiting examples.

Herein, control device 500 may control the stimulus device so as to shut off or reduce the stimulus being provided to a plurality of persons. For example, when stimulus device 600 is a light source, control device 500 may block (turn off) or reduce (lower the amount of light) of the light after stimulus device 600 has provided the light as a stimulus to a plurality of persons.

Now a relationship between near-infrared light source 100 and a person will be described with reference to FIG. 3 and FIG. 4.

Figure 3:
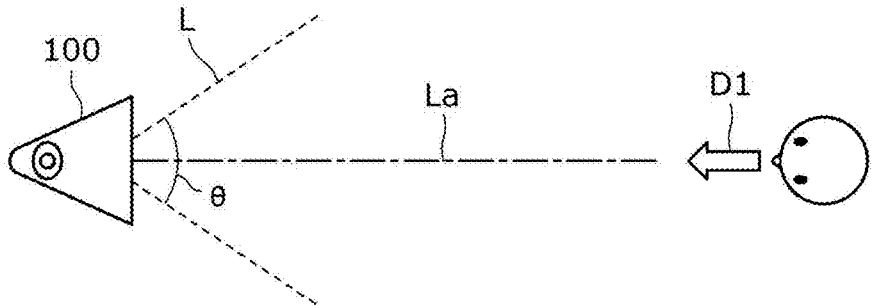
FIG. 3 is a schematic diagram of a near-infrared light source and a person according to an embodiment, as they are viewed in the vertical direction.
Figure 4:
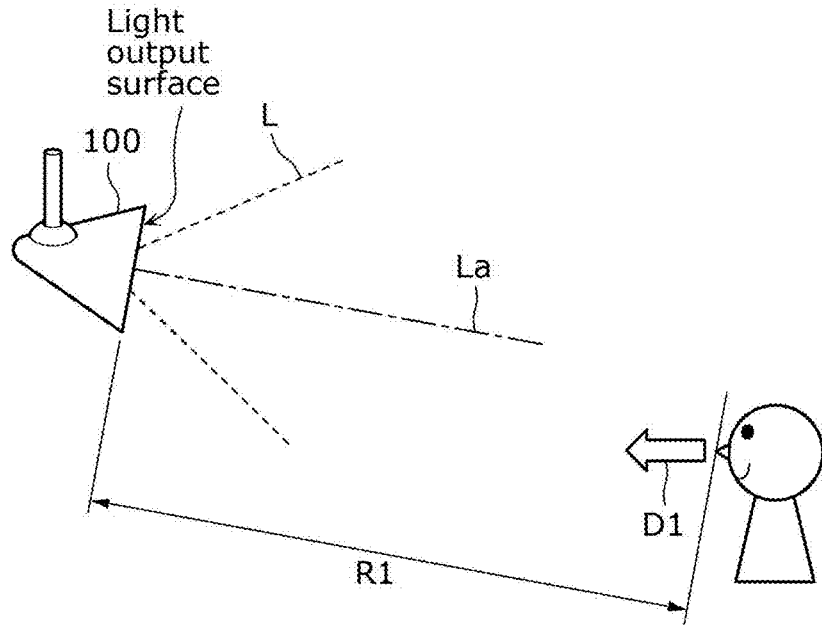
FIG. 4 is a schematic diagram of the near-infrared light source and the person shown in FIG. 3, as they are viewed from the side.

FIG. 3 is a schematic diagram of near-infrared light source 100 and a person according to the present embodiment, as they are viewed in the vertical direction. To be more specific, FIG. 3 is a diagram showing near-infrared light source 100 and a person among a plurality of persons, as they are viewed from the above in the vertical direction. In other words, FIG. 3 is a diagram showing near-infrared light source 100 and a person from above the head of the person. FIG. 4 is a schematic diagram of near-infrared light source 100 and the person shown in FIG. 3, as they are viewed from the side.

Now, forward direction D1 indicated in FIG. 3 and FIG. 4 will be described. Forward direction D1 is the direction that the head of at least one person among a plurality of persons faces. According to the present embodiment, near-infrared light source 100 outputs output light L toward one person from a direction other than forward direction D1 that the head of that one person faces. The first near-infrared radiation is emitted toward the one person from such a direction that the near-infrared radiation does not cast a shadow directly behind the face of the person facing the front. In other words, the first near-infrared radiation included in output light L is not emitted from forward direction D1 that the head (the face) of the one person faces. To rephrase, the first near-infrared radiation included in output light L is emitted toward the one person from above or below the face of the one person or emitted from a side (the right or the left) or obliquely from a side of the face of the one person.

In this example, optical axis La is taken as the angular direction in which the component of the first near-infrared radiation that has the highest radiation intensity travels. When the first near-infrared radiation included in output light L is emitted toward a person from a side or obliquely from a side of the face of the one person, optical axis La and forward direction D1 are not parallel. Meanwhile, when the first near-infrared radiation included in output light L is emitted toward one person from above or below the face of the one person, optical axis La and forward direction D1 may be parallel as they are viewed in the vertical direction, as indicated in FIG. 3.

In this manner, psychological state display system 1 according to the present embodiment does not have to emit the first near-infrared radiation from forward direction D1 of the face of a person.

Meanwhile, the area of the region irradiated with the first near-infrared radiation is greater than or equal to 10 m$^2$ and less than 10,000 m$^2$. This area is more preferably greater than or equal to 25 m$^2$ or even more preferably greater than or equal to 100 m$^2$.

In this example, there is no particular limitation on the upper limit of the area of the region irradiated with the first near-infrared radiation. This is because the imaging of the first near-infrared radiation is dependent on the amount of the first near-infrared radiation. Herein, if the upper limit is to be set in consideration of the reality of illumination technologies and imaging technologies, the upper limit may be around less than 10,000 m$^2$ as stated above.

This setting allows a plurality of persons in a large space to be irradiated with the first near-infrared radiation. In other words, the above setting can implement psychological state display system 1 that makes it possible to visualize a change in the psychological state of a plurality of persons present in a large space.

Now, distance R1 indicated in FIG. 4 will be described.

Distance R1 is the distance between near-infrared light source 100 and the person among a plurality of persons who is located closest to near-infrared light source 100. To be more specific, distance R1 is the distance between the light exiting surface of near-infrared light source 100 and the person among the plurality of persons who is located closest to near-infrared light source 100. The output surface is the surface through which output light L is outputted.

Distance R1 may be greater than or equal to 50 cm and less than 30 m. Meanwhile, distance R1 is greater than or equal to 50 cm and less than 3 m (a first illumination distance), greater than or equal to 3 m and less than 5 m (a second illumination distance), or greater than or equal to 5 m and less than 20 m (a third illumination distance).

When distance R1 is the first illumination distance, this configuration is convenient in visualizing the psychological state of a person, for example, in an office, a seminar room, a classroom, a store, a public space (e.g., a public office, a library, etc.), or a public transportation space (inside a train or inside a bus). When distance R1 is the second illumination distance, this configuration is convenient in visualizing the psychological state of a person, for example, in an indoor event space, a movie theater, a gymnasium, a small-scale outdoor event space, or a relatively small area in a city. When distance R1 is the third illumination distance, this configuration is convenient in visualizing the psychological state of a person, for example, in a large-scale outdoor event space, a sporting event space, or a relatively large area in a city.

Furthermore, it is preferable that the distance between near-infrared light source 100 and each of the plurality of persons be within the range stated above.

The light distribution pattern of the first near-infrared radiation can be selected from a narrow-angle light distribution where the light distribution angle is smaller than 15°, a mid-angle light distribution where the light distribution angle is greater than or equal to 15° and smaller than 30°, a wide-angle light distribution where the light distribution angle is greater than or equal to 30° and smaller than 90°, and a Lambertian light distribution.

As the light distribution pattern approaches the narrow-angle light distribution, the first near-infrared radiation becomes more like a beam. This can provide a light distribution pattern advantageous in irradiating a region far from near-infrared light source 100 with the first near-infrared radiation.

Meanwhile, as the light distribution pattern approaches the Lambertian light distribution, a more uniform and soft first near-infrared radiation can be emitted toward a broad range. This can provide a light distribution pattern advantageous in irradiating a broader range with the first near-infrared radiation.

Herein, near-infrared light source 100 may include a light distribution controlling mechanism (not shown) that controls the light distribution of the first near-infrared radiation to be outputted. In this case, the first near-infrared radiation can be made into a beam or made to have a Lambertian light distribution with the use of a lens and/or a mirror included in the light distribution controlling mechanism. This configuration makes it possible to emit a first near-infrared radiation suitable, for example, for generating psychological data.

Now, divergence angle θ of the first near-infrared radiation included in output light L in the horizontal direction as near-infrared light source 100 is viewed in the vertical direction as shown in FIG. 3 will be described.

Divergence angle θ means the range of angles at which the first near-infrared radiation having a radiation intensity in the same distance that is one half the maximum intensity is outputted. According to the present embodiment, divergence angle θ may be greater than or equal to 30° and smaller than or equal to 180° or more preferably greater than or equal to 45° and smaller than or equal to 120°. When divergence angle θ is within this range, a broad region far from near-infrared light source 100 can be irradiated with the first near-infrared radiation. Thus, the space needed for psychological state display system 1 can be reduced.

Processing Procedure of Psychological State Visualization Method

Next, a specific processing procedure of a psychological state visualization method executed by psychological state display system 1 will be described.

FIG. 5 is a flowchart showing a processing procedure through which psychological state display system 1 according to the present embodiment trains machine learning model 321.

First, trainer 330 obtains training data for training machine learning model 321 (S101). Herein, the training data may be generated by generator 320. This, however, is not a limiting example, and the training data may be generated by another processor or by another device.

The training data will be described below.

As stated above, the training data includes one or more data sets.

One data set is composed of a set of an infrared image captured by imaging device 200 and the psychological state of a person captured in the infrared image. For example, the infrared image captures the face and the body of the person. This infrared image is paired with one of the person's psychological states, including being happy, being sad, feeling energetic, being scared, being angry, feeling depressed, being alert, being absent-minded, being interested, and feeling nervous.

Herein, for the training data, visual data collected under visible light with the use of a visible light sensor can also be used.

After step S101 is performed, trainer 330 trains machine learning model 321 with the use of the training data obtained at step S101 (S102). To be more specific, trainer 330 trains machine learning model 321 through machine learning. Furthermore, trainer 330 outputs trained machine learning model 321 to generator 320.

After the processes in the flowchart shown in FIG. 5 are performed, a process of visualizing the psychological state of the person is performed by psychological state display system 1.

FIG. 6 is a flowchart showing a processing procedure through which psychological state display system 1 according to the present embodiment visualizes the psychological state of the person.

Near-infrared light source 100 outputs output light L including a first near-infrared radiation toward a plurality of persons (S201).

Imaging device 200 receives the first near-infrared radiation included in output light L outputted by near-infrared light source 100, and captures an infrared image of the plurality of persons (S202). In this operation example, imaging device 200 captures an infrared image at predetermined intervals, and imaging device 200, upon capturing one infrared image and outputting that infrared image to generation device 300, captures another infrared image and outputs that infrared image to generation device 300. In other words, imaging device 200 successively outputs a captured infrared image to generation device 300, and generation device 300 successively obtains the infrared image successively outputted by imaging device 200.

Generation device 300 generates psychological data indicating the psychological state of at least one person among the plurality of persons captured in the infrared image, with the use of machine learning model 321 that receives the infrared image as an input (S203).

In machine learning model 321, in response to receiving an input of the infrared image obtained by generation device 300, machine learning model 321 outputs the psychological state of at least one person among the plurality of persons captured in the infrared image. Generation device 300 generates psychological data indicating this psychological state.

Herein, each time generation device 300 obtains one infrared image, generation device 300 generates one item of psychological data corresponding to the obtained one infrared image. Since generation device 300 successively obtains an infrared image, as stated above, generation device 300 successively generates psychological data. Each time generation device 300 generates psychological data, generation device 300 outputs the generated psychological data to display device 400. In other words, display device 400 successively obtains generated psychological data.

Display device 400 displays the obtained psychological data (S204). Herein, since display device 400 successively obtains generated psychological data, as stated above, display device 400 successively displays psychological data. As stated above, imaging device 200 captures an infrared image at predetermined intervals. Therefore, in display device 400, after one item of psychological data that is based on one infrared image is displayed, the subsequent item of psychological data that is based on the subsequent infrared image captured after the predetermined time has passed since the capture of the one infrared image is displayed. In other words, display device 400 displays a change over time in the psychological data. To rephrase, display in display device 400 shows a manner in which the psychological state of the person changes every moment.

Now, psychological state display system 1 according to the present embodiment will be compared with the technology disclosed in Patent Literature 1.

Patent Literature 1 discloses a technology for displaying a temporary psychological state of a person. However, the psychological state of this person observed before or after the displayed psychological state is not clear. Furthermore, according to the disclosure in Patent Literature 1, a plurality of images (still images) are extracted from a moving image, the mean value of the plurality of images is calculated, and one psychological state is displayed based on the calculated mean value. Even in this case, since only one psychological state is displayed, it is not clear whether there has been a change in the psychological state of the person between the plurality of images.

The psychological state of a human (a person) naturally changes every moment. According to Patent Literature 1, although a temporary psychological state of a person is displayed, how the psychological state of this person changes is not displayed.

According to the present embodiment, the psychological state of a person that changes every moment is displayed, for example, as indicated at step S204 of FIG. 6. In other words, psychological state display system 1 according to the present embodiment can visualize a change over time in the psychological state of a person.

Furthermore, when an image used in the technology disclosed in Patent Literature 1 is a visible light image, this image is subject to an influence of illumination light (visible light) in the space where the image is captured. For example, the image quality or the like of the image is affected by the lighting of the illumination light in the space, and as a result, the psychological state to be displayed is also affected. In other words, according to the technology disclosed in Patent Literature 1, the psychological state displayed is affected by the illumination light (the visible light) in the space where the image is captured.

In contrast, psychological state display system 1 according to the present embodiment uses a first near-infrared radiation (an infrared image to be more specific) and visualizes a change over time in the psychological state of a person. Therefore, psychological state display system 1 is less likely to be affected by the illumination light (the visible light) in the space where psychological state display system 1 is used, when psychological state display system 1 visualizes a change in the psychological state of a person. In other words, the present embodiment can implement psychological state display system 1 that can visualize a change in the psychological state of a person under the condition where an influence of illumination light is minimized.

Now, psychological data will be described in greater detail with reference to FIG. 7 and FIG. 8.

Figure 7:
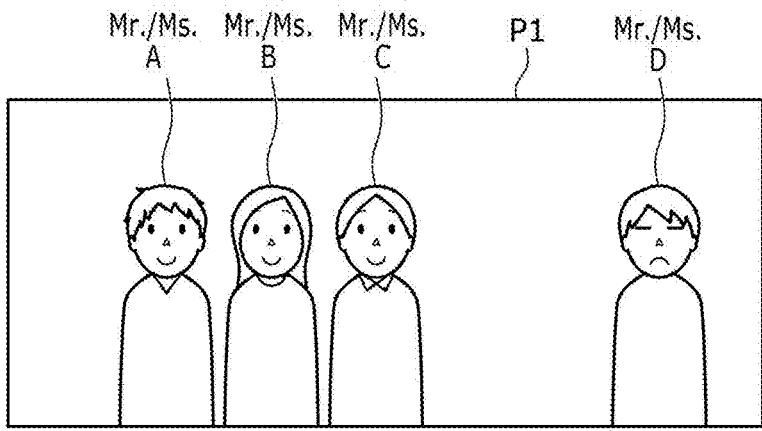
FIG. 7 is a diagram showing an infrared image captured by an imaging device according to an embodiment.

FIG. 7 is a diagram showing infrared image P1 captured by imaging device 200 according to the present embodiment.

Figure 8:
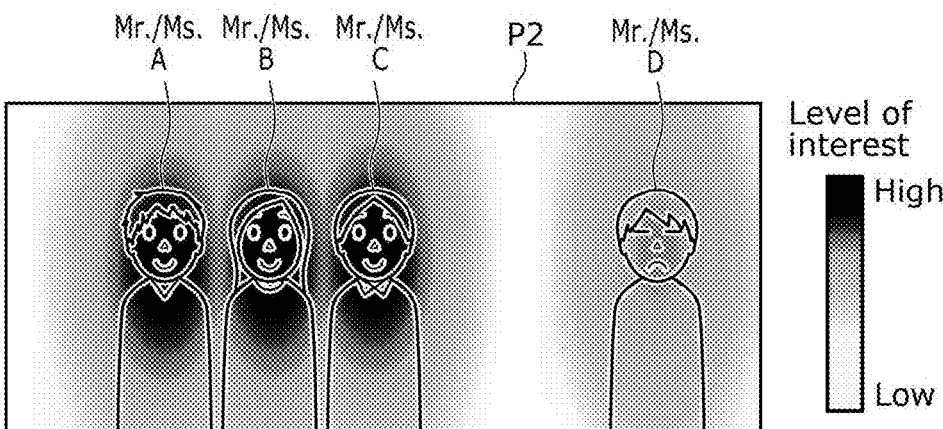
FIG. 8 shows one example of psychological data that is based on the infrared image shown in FIG. 7.

FIG. 8 shows one example of psychological data that is based on infrared image P1 shown in FIG. 7.

Infrared image P1 shown in FIG. 7 includes a plurality of persons, or more specifically, includes four persons: Mr./Ms. A. Mr./Ms. B, Mr./Ms. C, and Mr./Ms. D.

As stated above, in machine learning model 321, in response to receiving an input of infrared image P1, machine learning model 321 may output the psychological state of at least one person among the four persons. In this example, machine learning model 321 outputs the psychological state of each of the four persons (i.e., every person). In other words, the psychological data shown in FIG. 8 indicates the psychological state of each of the four persons.

Herein, as the psychological state, the level of interest indicating how much each person is feeling interested is used. In FIG. 8, the level of interest of each of the four persons is shown as the psychological data.

Herein, the number of levels of the psychological state displayed is preferably greater than or equal to 2 and less than or equal to 11 or is more preferably less than or equal to 6. For example, when the number of levels of the level of interest is 6, the display indicates that, from the higher level of interest, the level of interest is 5, the level of interest is 4, the level of interest is 3, the level of interest is 2, the level of interest is 1, and the level of interest is 0, for example. Not only the number of levels of the level of interest, but also the number of levels of other psychological states (e.g., the number of levels of joy) is preferably greater than or equal to 2 and less than or equal to 11 or is preferably less than or equal to 6.

When the number of levels displayed is within the stated range in this manner, this configuration makes it possible to roughly grasp the psychological state of each of a plurality of persons and to reduce the amount of data to be handled. Accordingly, this configuration is advantageous in reducing the size of the device used as psychological state display system 1 and in improving the data processing speed.

As stated above, examples of the psychological data include displaying data such as numerical value displaying data, color displaying data, pattern displaying data, graphical symbol displaying data, emoji displaying data, and illustration displaying data. Furthermore, according to the present embodiment, the psychological data is image data in which at least one of the items of data listed above is superposed on a captured infrared image. When the psychological data is image data, the image data is displayed on display device 400 with the plurality of persons captured in the infrared image and the corresponding psychological states of these persons mapped to each other.

Using numerical value displaying data is advantageous in displaying psychological states finely and in representing psychological states in numerical values. Using color displaying data is advantageous in representing psychological states in colors. Using pattern displaying data, graphical symbol displaying data, or emoji displaying data is advantageous in symbolically representing psychological states in the form of figures and pattern symbols. The mode of displaying psychological states in illustration displaying data is advantageous in representing psychological states in illustrations. Furthermore, using image data is advantageous in representing psychological state of a person mapped to that person.

Now, an example in which color displaying data is used will be described with reference to FIG. 8.

FIG. 8 shows image data P2 in which color displaying data is superposed on captured infrared image P1.

With regard to the psychological data shown in FIG. 8, the colors corresponding to the respective psychological states of the four persons are displayed. The darker the color is, the higher the level of interest is, and the lighter the color is, the lower the level of interest is. In FIG. 8, a dark color is superposed on Mr./Ms. A, Mr./Ms. B, and Mr./Ms. C, and this indicates that their levels of interest are high. Meanwhile, a light color is superposed on Mr./Ms. D, and this indicates that his/her level of interest is low. Although FIG. 8 uses the darkness of a color to represent the corresponding psychological state, the colors may be expressed in actual colors.

In this manner, it is convenient that the psychological state of a person is displayed, in particular, in a color (a color tone). When a psychological state is displayed, in particular, in a color, this configuration allows a mode of display in which, distinctively, an excited state is displayed in red, a somewhat excited state is displayed in yellow, a somewhat calm state is displayed in green, a calm state is displayed in blue, and a depressed state is displayed in gray or black. In this manner, psychological state display system 1 according to the present embodiment can visualize a change over time in the psychological state of a person with the use of colors. Therefore, a user who looks at display device 400, for example, can intuitively understand a change over time in the psychological state of the person.

Furthermore, as stated above, the number of levels of the psychological state displayed is preferably less than or equal to 6. For example, when the number of levels is 6, if a psychological state of a person is displayed in rainbow colors, this display allows a user to more easily understand a change over time in the psychological state of the person.

Now, another example of psychological data will be described with reference to FIG. 9.

Figure 9:
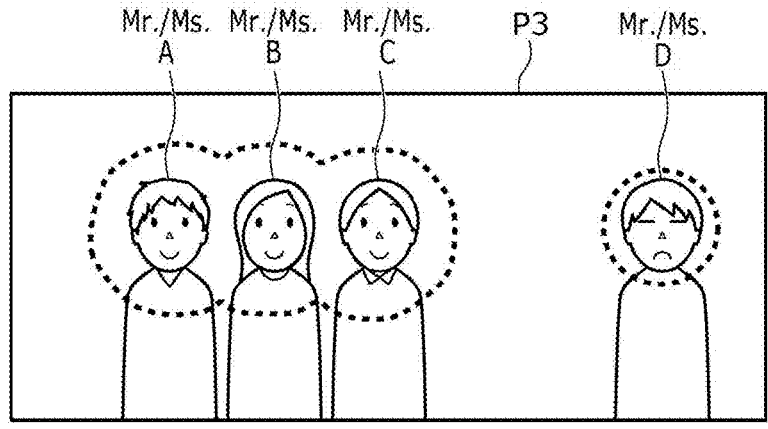
FIG. 9 shows another example of psychological data that is based on the infrared image shown in FIG. 7.

FIG. 9 shows another example of psychological data that is based on infrared image P1 shown in FIG. 7. To be more specific, FIG. 9 shows image data P3 in which graphical symbol displaying data is superposed on captured infrared image P1.

With regard to the psychological data shown in FIG. 9, the graphical symbols corresponding to the respective psychological states of the four persons are displayed. A graphical symbol is a display item and is a dashed frame shown in FIG. 9. In the drawing, the larger the frame is, the higher the level of interest is, and the smaller the frame is, the lower the level of interest is. In other words, the size of the area of the display item expresses the level of interest. In FIG. 9, a large frame is superposed on Mr./Ms. A, Mr./Ms. B, and Mr./Ms. C, and this indicates that their levels of interest are high. Meanwhile, a small frame is superposed on Mr./Ms. D, and this indicates that his/her level of interest is low. Herein, the level of interest may be indicated with a different graphical symbol.

When graphical symbol displaying data is used as shown in FIG. 9, the psychological state of a person is displayed prominently. In this manner, psychological state display system 1 according to the present embodiment can visualize a change over time in the psychological state of a person with the use of a graphical symbol. Therefore, a user who looks at display device 400, for example, can intuitively understand a change over time in the psychological state of the person.

Now, another example of psychological data will be described with reference to FIG. 10.

Figure 10:
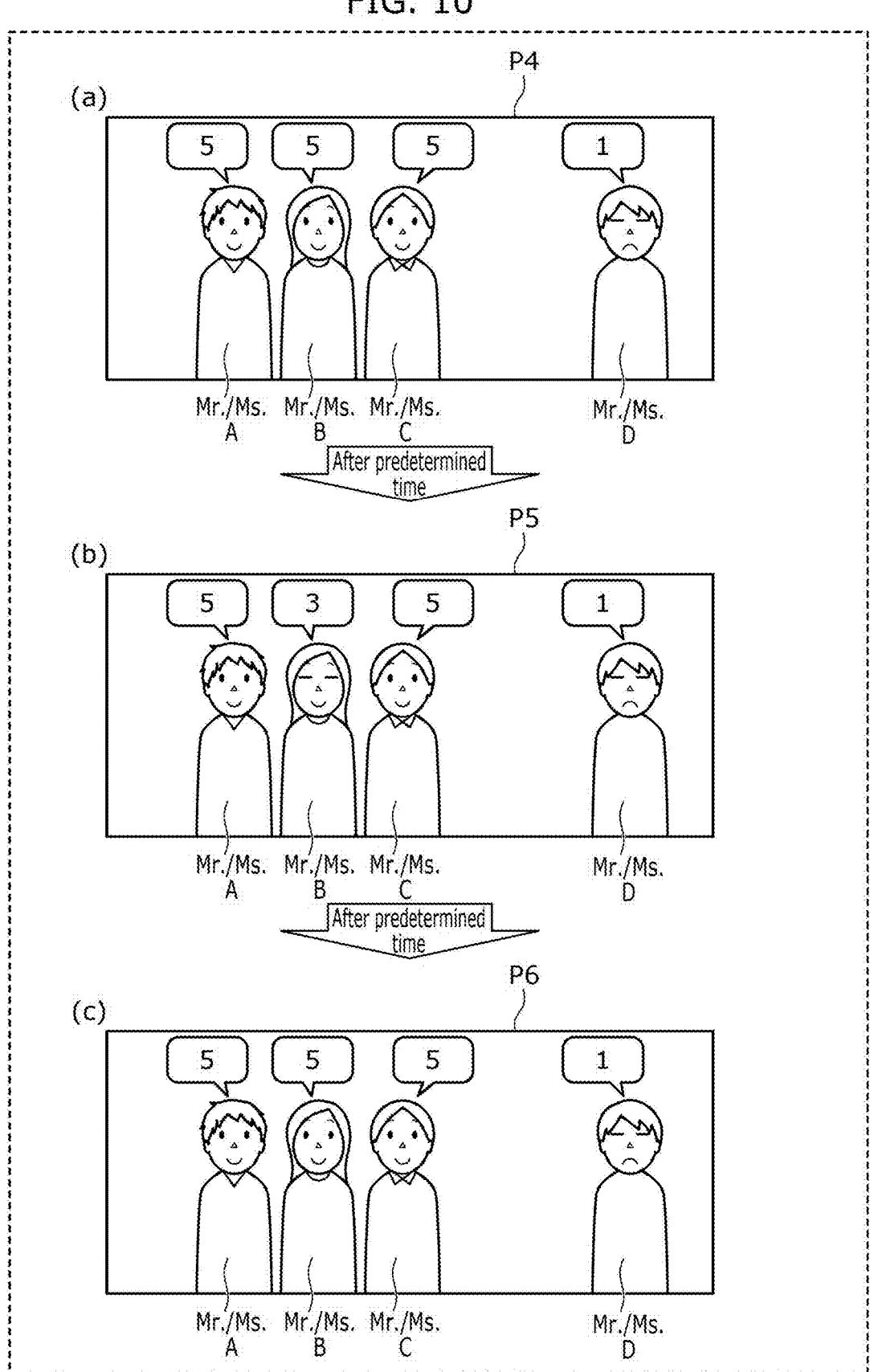
FIG. 10 shows yet another example of psychological data according to an embodiment.

FIG. 10 shows another example of psychological data according to the present embodiment.

To be more specific, FIG. 10 shows image data in which numerical value displaying data is superposed on a captured infrared image. In FIG. 10, (a) shows image data P4 in which numerical value displaying data, or psychological data that is based on infrared image P1, is superposed on captured infrared image P1. In FIG. 10, (b) shows image data P5 regarding psychological data that is based on an infrared image captured after a predetermined time has passed since the capturing of infrared image P1. In FIG. 10, (c) shows image data P6 regarding psychological data that is based on an infrared image captured after a predetermined time has passed since the capturing of the infrared image in (b) of FIG. 10. In other words, FIG. 10 is a diagram showing, for example, a change over time in the psychological data displayed in display device 400 at step S204 of FIG. 6.

With regard to the psychological data shown in FIG. 10, the numerical values corresponding to the respective psychological states of the four persons are displayed. In this display, the number of levels of the level of interest, or the psychological state, is 6, and the display indicates that, from the higher level of interest, the level of interest is 5, the level of interest is 4, the level of interest is 3, the level of interest is 2, the level of interest is 1, and the level of interest is 0. In (a) and (c) of FIG. 10, "the level of interest is 5" is superposed on Mr./Ms. A, Mr./Ms. B, and Mr./Ms. C, and this indicates that their levels of interest are high. Meanwhile, "the level of interest is 1" is superposed on Mr./Ms. D, and this indicates that his/her level of interest is low. In (b) of FIG. 10, "the level of interest is 5" is superposed on Mr./Ms. A and Mr./Ms. C, and this indicates that their levels of interest are high; "the level of interest is 3" is superposed on Mr./Ms. B, and this indicates that his/her level of interest is medium; and "the level of interest is 1" is superposed on Mr./Ms. D, and this indicates that his/her level of interest is low.

Using numerical value displaying data, as shown in FIG. 10, makes it easier to finely display the psychological states and to represent the psychological states in numerical values. In this manner, psychological state display system 1 according to the present embodiment can visualize a change over time in the psychological state of a person with the use of numerical values. Therefore, a user who looks at display device 400, for example, can intuitively understand a change over time in the psychological state of the person.

In FIG. 8 to FIG. 10, image data in which at least one of the various items of displaying data serving as psychological data is superposed on a captured infrared image is used, but this is not a limiting example.

For example, when numerical value displaying data alone is used as psychological data, psychological data that is based on infrared image P1 may be document data that includes numerical values that states, for example, that "the level of interest of Mr./Ms. A, Mr./Ms. B, and Mr./Ms. C is 5, and the level of interest of Mr./Ms. D is 1".

According to the present embodiment, psychological data indicating the psychological state of each of a plurality of persons is displayed, but this is not a limiting example. For example, psychological data indicating a mean value of the psychological states of a plurality of persons may be displayed. In this case, for the psychological data corresponding to the one shown in (a) of FIG. 10, data stating, for example, that "the level of interest of the plurality of persons is 4" may be used.

Such a configuration makes it possible to implement psychological state display system 1 that can visualize a change over time in an average psychological state of a plurality of persons.

Furthermore, when numerical value displaying data is used as psychological data, the numerical values indicating the levels of interest may be integrated, and the resultant numerical value may be displayed. For example, when the numerical values indicating the levels of interest shown in (a) to (c) of FIG. 10 are integrated, the results are 15 for Mr./Ms. A and for Mr./Ms. C, 13 for Mr./Ms. B, and 3 for Mr./Ms. D, and these numerical values are displayed on display device 400.

Such a configuration makes it possible to implement psychological state display system 1 that can visualize the psychological state of each person held over a predefined period.

Furthermore, when numerical value displaying data is used as psychological data, the numerical values indicating the levels of interest may be differentiated, and the resultant numerical value may be displayed.

Such a configuration makes it possible to implement psychological state display system 1 that can visualize a change over time in the psychological state of a person held over a short period of time.

Now, referring back to FIG. 6, the process will be further described.

Based on the generated psychological data, generation device 300 determines a stimulus to be provided to the plurality of persons (S205). Herein, generation device 300 may determine to provide a stimulus to all of the plurality of persons or may determine to provide a stimulus to one or more of the plurality of persons.

Furthermore, when the psychological data generated by generation device 300 indicates that the psychological state of one or more persons is a predetermined psychological state, generation device 300 may determine a stimulus to be provided to the one or more persons, based on this predetermined psychological state.

This configuration can limit the person or persons to whom to provide a stimulus to change his/her psychological state, and renders it unnecessary to provide a stimulus to a person or persons, among the plurality of persons, who are not to be subjected to the stimulus. Accordingly, the configuration above makes it possible to implement psychological state display system 1 that can efficiently control the psychological state of a person to be targeted.

Now, a predetermined psychological state and a stimulus will be described.

For example, when the predetermined psychological state is that "the level of interest is lower than or equal to 1", the stimulus to be provided to the one or more persons is light. As shown in FIG. 10, the psychological state of Mr./Ms. D, who is one person, is that "the level of interest is lower than or equal to 1", and in this case, generation device 300 determines light as the stimulus to be provided to Mr./Ms. D. In this case, stimulus device 600 is a light source device that emits this light (visible light to be more specific).

Communicator 310 of generation device 300 outputs stimulus data indicating the determined stimulus to control device 500. Control device 500 obtains the stimulus data outputted thereto.

Control device 500 controls stimulus device 600 based on the obtained stimulus data (S206). For example, control device 500 performs control of causing the stimulus device, constituted by a light source device, to emit the light toward Mr./Ms. D. This light emission is expected to change the psychological state of Mr./Ms. D and, for example, to improve his/her level of interest. In this case, there is no need to provide a stimulus to Mr./Ms. A, Mr./Ms. B, or Mr./Ms. C. In other words, the configuration above can provide a stimulus efficiently to Mr./Ms. D alone.

In the example described above, generation device 300 determines to provide a stimulus to one or more of the plurality of persons (i.e., to Mr./Ms. D), and control device 500 controls stimulus device 600 so as to provide the determined stimulus to at least the part of the plurality of persons. This, however, is not a limiting example. Generation device 300 may determine to provide a stimulus to all of the plurality of persons (e.g., to Mr./Ms. A, Mr./Ms. B, Mr./Ms. C, and Mr./Ms. D), and control device 500 may control stimulus device 600 so as to provide the stimulus to all of the plurality of persons.

Herein, generation device 300 may determine a stimulus to be provided to a part or all of the plurality of persons, based on a change over time in the psychological state indicated by generated psychological data. In FIG. 10, while there is no change over time in the psychological state of Mr./Ms. A, Mr./Ms. C, and Mr./Ms. D and their levels of interest remain constant over time, the psychological state of Mr./Ms. B changes over time and his/her level of interest changes. In this case, for example, generation device 300 may determine to provide a stimulus to Mr./Ms. A, Mr./Ms. C, and Mr./Ms. D, who show no change over time in their psychological states, and may determine to provide a stimulus to Mr./Ms. B, who shows a change over time in his/her psychological state.

Although light is used as a stimulus in the case above in which the psychological state indicates that "the level of interest is lower than or equal to 1", this is not a limiting example. For example, other examples are described below.

In another example, as stated above, when there is a suspicious person whose psychological state indicates "a state of being nervous", a stimulus may be determined that can prevent a criminal activity (e.g., light that brightly illuminates this suspicious person, or a sound (an audio) stating that "the police are on patrol").

In yet another example, when a stimulus such as a sound or light is controlled in accordance with the level of interest indicative of a psychological state while psychological state display system 1 is used in an entertainment space, such control can liven up the event or heighten the emotions of the persons in that space. Conversely, to a person having difficulty keeping his/her emotions under control, a calming stimulus may be provided.

Display device 400 according to the present embodiment may display vitals information of a person. For example, at step S204 of FIG. 6, the psychological data and the vitals information of the person may be displayed. In this case, the vitals information may be obtained, for example, in the following manner. Imaging device 200 captures an infrared image that includes blood vessel information indicating vasoconstriction of each of a plurality of persons. Based on the blood vessel information included in the captured infrared image, generation device 300 generates vitals information indicating the vital signs of at least one person among the plurality of persons.

The blood vessel information is, for example, information on the optical reflectance of the skin of a person captured in an infrared image. Meanwhile, the vital signs include, for example, the heart rate. Since blood has a property of absorbing light, the optical reflectance changes in accordance with the vasoconstriction caused by pulse waves. Therefore, based on the information on the optical reflectance of a person's skin (blood vessel information), pulse waves are estimated, and the heart rate is calculated. The vitals information is information that indicates the heart rate (a vital sign) of the person.

Furthermore, display device 400 displays the generated vitals information. In one example, when displaying image data P2 shown in FIG. 8, display device 400 may display the vitals information superposed on image data P2.

With this configuration, psychological state display system 1 can not only visualize a change over time in the psychological state of the person but also visualize the vitals information of the person and a change over time in that vitals information.

Now, a space in which psychological state display system 1 is used and advantageous effects obtained in that space will be described in greater detail.

As described above, psychological state display system 1 is, in one example, a system that is used in a space such as an entertainment space, a public space, or a learning space. An entertainment space, a public space, or a learning space is often a relatively large space.

Herein, an entertainment space includes a space such as (1) or (2) below. (1) A stage lighting illuminated space (e.g., a live event space or an affordance illumination space) where the state of illumination by visible light changes rapidly. (2) A dark space or a dimmed space (e.g., a movie theater, a bar, or a karaoke house) where a person enjoys a video image or sound effects). Herein, an affordance illumination space is an outdoor stage lighting illuminated space where illuminating light, with added movements, dimming, and color changes, provides stage lighting evoking the sense of liveliness within the space to influence the psychological state and actions ("circling around" and "staying") of a human.

Meanwhile, a public space means to include a space within a public transportation vehicle (e.g., a train, a bus, a taxi, or an airplane) and includes, for example, a space described in (3) below. (3) A traveling space overnight where entering and blocking of outside light, such as the sunlight, are repeated, or a traveling space (e.g., the inside of a bus traveling on an expressway) where a dark place (e.g., inside a tunnel) and a bright space alternate.

Meanwhile, a learning space includes a space where a person studies, such as a home, a school, an after-school learning center, or a seminar room, and such a space has the person studying and may further have another person (e.g., a lecturer) who guides the studying. Psychological state display system 1 may be used in, among the learning spaces, a space described in (4) below, in particular. (4) At least one illumination space illuminated with white illumination light of different light colors (e.g., different chromaticity).

In an entertainment space and a public space (in particular, the spaces described in (1), (2), and (3) above), the presence, the intensity, and the color tone of the visible light in such a space easily change to a great extent, and the psychological state of a person in such a space tends to fluctuate easily. According to the present embodiment, a change in the psychological state of a person is visualized with the use of a first near-infrared radiation (an infrared image to be more specific). In other words, even if the presence, the intensity, and the color tone of the visible light changes to a great extent in such a space, psychological state display system 1, since it uses a first near-infrared radiation in a wavelength range different from the wavelength range of visible light, can easily visualize a change in the psychological state of a person whose psychological state tends to fluctuate easily.

Furthermore, in a learning space like the one described in (4) in particular, if, for example, the psychological state of a person is estimated with the use of visible light and a visible light image that is based on this visible light when the person is irradiated with a plurality of rays of white illumination light of different chromaticity, the accuracy of estimation may decreases depending on the chromaticity. Even in such a learning space, psychological state display system 1 according to the present embodiment, since it uses a first near-infrared radiation, can easily visualize a change in the psychological state of a person. Similar advantageous effects can be expected not only in a learning space but in any spaces like the one described in (4).

In this manner, the configuration above makes it possible to implement psychological state display system 1 that can easily visualize a change in the psychological state of a person even in a space where the presence, the intensity, and the color tone of visible light easily change to a great extent or a space where a person is irradiated with a plurality of rays of white illumination light of different chromaticity. In particular, psychological state display system 1 makes it possible to promptly detect a suspicious person or the like in such an environment, and the use of stimulus device 600 makes it possible to prevent a crime. Accordingly, psychological state display system 1 configured as described above is a system expected to advantageously solve social problems by revitalizing economy, solving inequalities, and making the society safer.

Now, psychological state display system 1 according to the present embodiment will be compared with existing technologies.

For example, Patent Literature 2 (Japanese Unexamined Patent Application Publication No. 2009-87303) discloses a technology that estimates a facial expression indicating, for example, an anxiety or a surprise of the driver inside a vehicle. Meanwhile, Patent Literature 3 (Japanese Unexamined Patent Application Publication No. 2020-48149) discloses a technology that displays an emotion of a participant in an online meeting in a conference room.

The technology disclosed in Patent Literature 2 is applied to a small space, such as inside a vehicle, and it is difficult to apply that technology to a large space like an entertainment space or a public space (in particular, the spaces described in (1), (2), and (3) above).

Meanwhile, a conference room or the like where the technology disclosed in Patent Literature 3 is used is often a typical white illuminated space, and thus it is difficult to apply the technology disclosed in Patent Literature 3 to a space like the one described in (4) above.

In contrast, psychological state display system 1 according to the present embodiment can easily visualize a change in the psychological state of a person even in an entertainment space, a public space, or a learning space (in particular, the space described in (1), (2), (3), or (4) above), as described above.

Variations

Now, a variation of the embodiment will be described. Variation 1 of the embodiment differs from the embodiment in that the stimulus device is served by near-infrared light source 100a. The following description centers on the differences from the embodiment, and the description of the shared features will be omitted or simplified.

An example of a configuration of psychological state display system 1a according to Variation 1 of the embodiment will be described with reference to FIG. 11.

Figure 11:
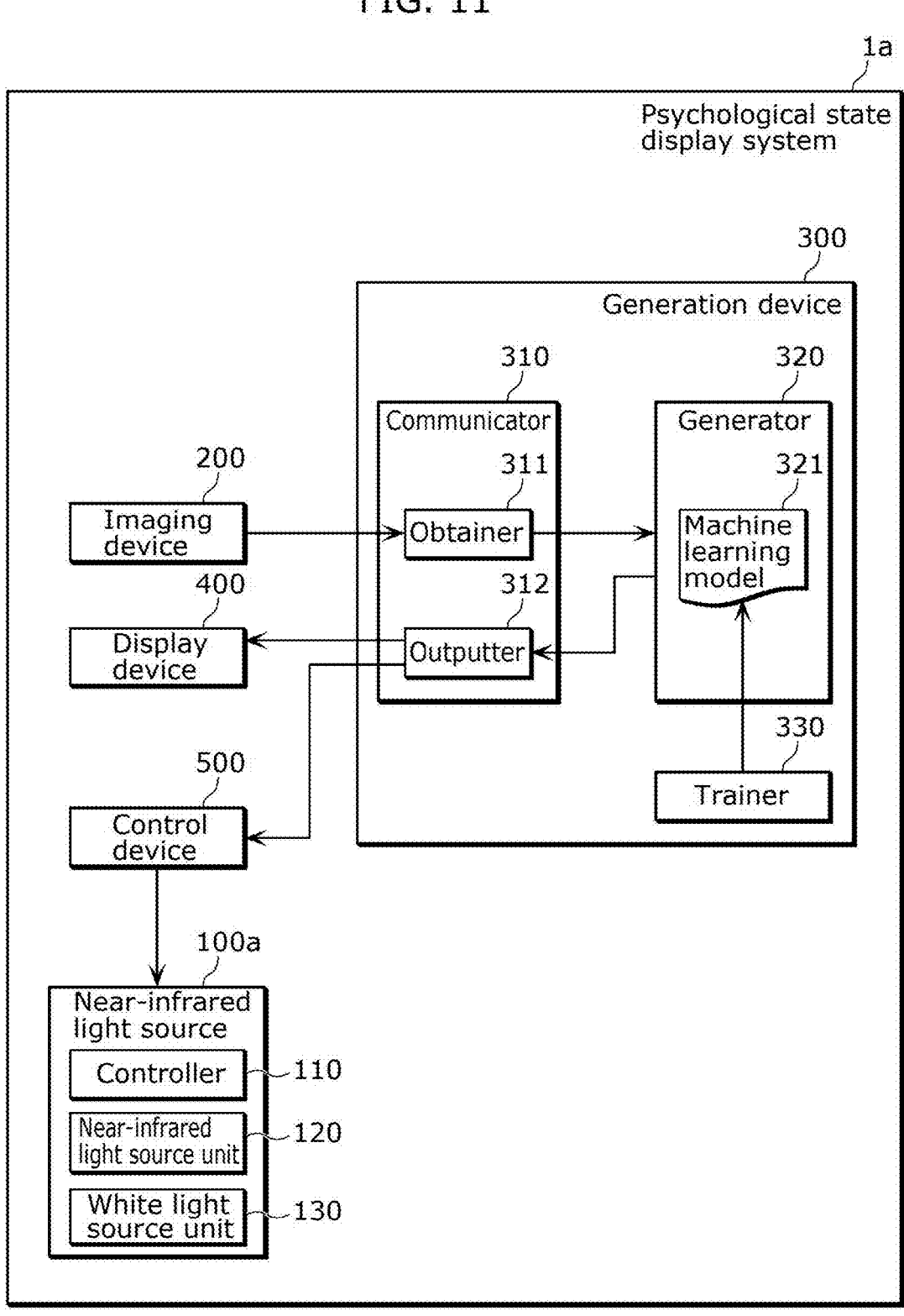
FIG. 11 is a block diagram showing a characteristic functional configuration of a psychological state display system according to a variation of an embodiment.

FIG. 11 is a block diagram showing a characteristic functional configuration of psychological state display system 1a according to Variation 1 of the present embodiment.

Psychological state display system 1a includes near-infrared light source 100a, imaging device 200, generation device 300, display device 400, and control device 500.

According to the present variation, the stimulus device is served by near-infrared light source 100a that outputs output light L including visible light. Meanwhile, generation device 300 determines a stimulus to be provided to a plurality of persons based on generated psychological data, and control device 500 controls the stimulus device (near-infrared light source 100a) so as to provide the determined stimulus to the plurality of persons. In this example, the visible light that near-infrared light source 100a outputs is determined as the stimulus, and this visible light is outputted toward the plurality of persons.

This configuration can reduce the number of components of psychological state display system 1a according to the present variation and can simplify the configuration of psychological state display system 1a.

Advantageous Effects and Others

Psychological state display system 1 according to the present embodiment includes near-infrared light source 100, imaging device 200, generation device 300, and display device 400. Near-infrared light source 100 outputs, toward a plurality of persons, output light L including a first near-infrared radiation having a wavelength of greater than or equal to 780 nm and less than 2,500 nm. Imaging device 200 receives the first near-infrared radiation included in outputted output light L, and captures an infrared image of the plurality of persons. Generation device 300 generates psychological data indicating a psychological state, with the use of trained machine learning model 321 that, in response to receiving a captured infrared image as an input, outputs the psychological state of at least one person among the plurality of persons included in the infrared image. Display device 400 displays a change over time in the generated psychological data.

With this configuration, as indicated at step S204 of FIG. 6, for example, in display device 400, after one item of psychological data that is based on one infrared image is displayed, the subsequent item of psychological data that is based on the subsequent infrared image captured after a predetermined time has passed since the capture of the one infrared image is displayed. In other words, display in display device 400 shows the manner in which the psychological state of the person changes every moment. When an administrator or the like of psychological state display system 1 looks at the displayed change over time in the psychological data, the administrator or the like can understand the change in the psychological state of the plurality of persons and so on. In other words, psychological state display system 1 can visualize a change in the psychological state of a person.

Furthermore, psychological state display system 1 according to the present embodiment uses a first near-infrared radiation (an infrared image to be more specific) and visualizes a change over time in the psychological state of a person. Therefore, psychological state display system 1 is less likely to be affected by the illumination light (the visible light) in the space where psychological state display system 1 is used, when visualizing a change in the psychological state of the person. In other words, the present embodiment makes it possible to implement psychological state display system 1 that can visualize a change in the psychological state of a person under the condition where an influence of illumination light is minimized.

Furthermore, for example, the first near-infrared radiation has a peak wavelength in the range of wavelengths greater than or equal to 780 nm and less than 2,500 nm.

Thus, the first near-infrared radiation largely containing an infrared radiation component that is not visible to human eyes (the person's eyes) is emitted. Therefore, the configuration above makes it possible to implement psychological state display system 1 that can visualize a change in the psychological state of a person without causing any sense of discomfort in the person.

Furthermore, for example, near-infrared light source 100 includes a first solid-state light emitting element that outputs the first near-infrared radiation.

This configuration makes it possible to convert the electric energy to the first near-infrared radiation (optical energy), which in turn makes it possible to easily obtain an intense first near-infrared radiation. Accordingly, an infrared image capturing a plurality of persons with a higher accuracy can be captured with imaging device 200. Thus, the configuration above makes it possible to implement psychological state display system 1 that can visualize a change in the psychological state of a person with a higher accuracy.

Furthermore, for example, near-infrared light source 100 includes a second solid-state light emitting element that outputs excitation light and a phosphor member that, based on the outputted excitation light, outputs wavelength-converted light as the first near-infrared radiation.

This configuration can reduce non-uniformity of the spectral distribution and the intensity of the first near-infrared radiation. Accordingly, an infrared image capturing a plurality of persons with a higher accuracy can be captured with imaging device 200. Thus, the configuration above makes it possible to implement psychological state display system 1 that can visualize a change in the psychological state of a person with a higher accuracy.

Furthermore, for example, output light L includes visible light.

This configuration makes it possible to emit output light L that includes visible light that is visible to human eyes (the person's eyes). Accordingly, this configuration makes it possible to implement psychological state display system 1 that is advantageous in recognizing the presence of near-infrared light source 100 outputting the first near-infrared radiation.

Furthermore, for example, near-infrared light source 100 controls the first near-infrared radiation and the visible light independently of each other, and controls at least one of the on/off or the dimming of each of the first near-infrared radiation and the visible light.

As near-infrared light source 100 controls the first near-infrared radiation and the visible light in this manner, this control makes it possible to implement psychological state display system 1 for displaying a psychological state that is advantageous in visualizing a psychological state based on the first near-infrared radiation and in freely controlling the stage lighting effects that are based on the visible light.

Furthermore, for example, the received light signal intensity obtained as imaging device 200 receives the first near-infrared radiation reflected by the plurality of persons while output light L that includes the first near-infrared radiation is being outputted is referred to as the first received light signal intensity. A second near-infrared radiation different from the first near-infrared radiation is outputted toward the plurality of persons while output light L that includes the first near-infrared radiation is not being outputted. The received light signal intensity obtained as imaging device 200 receives the second near-infrared radiation reflected by the plurality of persons is referred to as the second received light signal intensity. The minimum value of the first received light signal intensity is greater than the maximum value of the second received light signal intensity.

With this configuration, the intensity of the second received light signal, which can result in noise in the signal for recognizing the plurality of persons, can be kept sufficiently small. As such noise can be kept sufficiently small, an infrared image capturing the plurality of persons with a higher accuracy can be captured with imaging device 200. Thus, the configuration above makes it possible to implement psychological state display system 1 that can visualize a change in the psychological state of a person with a higher accuracy.

Furthermore, for example, near-infrared light source 100 outputs output light L toward one person from a direction other than the forward direction that the head of at least one person among the plurality of persons faces.

Even when the person is not irradiated with the first near-infrared radiation from forward direction D1 that the face of the person faces in this manner, psychological state display system 1 can visualize a change in the psychological state of the person. For example, when psychological state display system 1 is used in a large space and a plurality of persons in that large space each move differently, each person cannot be irradiated with the first near-infrared radiation from forward direction D1 that the face of the person faces. Even in such a case, the configuration described above makes it possible to implement psychological state display system 1 that can visualize a change in the psychological state of a person.

Herein, as described above, an infrared image used when trainer 330 trains machine learning model 321 may capture the entire face or the entire body of a person. This, however, is not a limiting example, and it suffices that such an infrared image capture, for example, a part of the face or a part of the body of a person. As training is performed with the use of an infrared image that captures a part of the face or a part of the body of a person, psychological state display system 1 can visualize a change in the psychological state of the person even when the person is not irradiated with the first near-infrared radiation from forward direction D1 that the face of the person faces.

Furthermore, for example, the area of the region irradiated with the first near-infrared radiation is greater than or equal to 10 m² and less than 10,000 m².

This setting allows a plurality of persons in a large space to be irradiated with the first near-infrared radiation. In other words, the above setting makes it possible to implement psychological state display system 1 that can visualize a change in the psychological state of a plurality of persons in a large space.

Furthermore, for example, the distance between near-infrared light source 100 and the person among the plurality of persons who is located closest to near-infrared light source 100 is greater than or equal to 50 cm and less than 30 m.

Meanwhile, distance R1 is greater than or equal to 50 cm and less than 3 m (the first illumination distance), greater than or equal to 3 m and less than 5 m (the second illumination distance), or greater than or equal to 5 m and less than 20 m (the third illumination distance).

When distance R1 is the first illumination distance, this setting is convenient in visualizing the psychological state of a person, for example, in an office, a seminar room, a classroom, a store, a public space (e.g., a public office, a library, etc.), or in a public transportation space (inside a train or inside a bus). When distance R1 is the second illumination distance, this setting is convenient in visualizing the psychological state of a person, for example, in an indoor event space, a movie theater, a gymnasium, a small-scale outdoor event space, or a relatively small area in a city. When distance R1 is the third illumination distance, this setting is convenient in visualizing the psychological state of a person, for example, in a large-scale outdoor event space, a sporting event space, or a relatively large area in a city.

Furthermore, for example, when near-infrared light source 100 is viewed in the vertical direction, the divergence angle of the first near-infrared radiation in the horizontal direction is greater than or equal to 30° and smaller than or equal to 180°.

When divergence angle θ is within this range, a range of regions far from near-infrared light source 100 can be irradiated with the first near-infrared radiation. Thus, the space needed for psychological state display system 1 can be reduced.

Furthermore, for example, generation device 300 determines a stimulus to be provided to a plurality of persons, based on generated psychological data.

With this configuration, a stimulus for changing a person's psychological state can be determined in accordance with the psychological state of that person.

Furthermore, for example, psychological state display system 1 includes control device 500 that controls stimulus device 600 that provides a stimulus to a plurality of persons. Control device 500 controls stimulus device 600 so as to provide the determined stimulus to the plurality of persons.

This configuration makes it possible to implement psychological state display system 1 that can provide, to a person, a stimulus for changing the psychological state of that person in accordance with his or her psychological state and thus can control the psychological state of that person.

Furthermore, for example, psychological state display system 1 includes stimulus device 600. Control device 500 controls stimulus device 600 so as to provide the determined stimulus to at least one or more of the plurality of persons.

This configuration makes it possible to provide a stimulus to at least one or more persons among the plurality of persons and thus makes it possible to implement psychological state display system 1 that can control the psychological state of the one or more persons.

Furthermore, for example, the determined stimulus is a stimulus that acts on at least one of the vision, the hearing, the smell, or the touch of the plurality of persons.

This configuration, by providing a stimulus to the five senses excluding the taste of the plurality of persons, makes it possible to implement psychological state display system 1 that can change the psychological state of the plurality of persons.

Furthermore, for example, control device 500 controls stimulus device 600 so as to shut off or reduce the stimulus being provided to a plurality of persons.

This configuration makes it possible to implement psychological state display system 1 that can change the psychological state of the plurality of persons by softening the stimulus being provided to the plurality of persons.

Furthermore, for example, when the generated psychological data indicates that the psychological state of one or more persons is a predetermined psychological state, generation device 300 determines a stimulus to be provided to the one or more persons based on this predetermined psychological state.

This configuration can limit the person or persons to whom a stimulus is provided to change the psychological state, and renders it unnecessary to provide a stimulus to a person or persons, among the plurality of persons, who are not to be subjected to the stimulus. Accordingly, the configuration above makes it possible to implement psychological state display system 1 that can efficiently control the psychological state of a person to be targeted.

Furthermore, for example, according to the variation, the stimulus device is served by near-infrared light source 100a that outputs output light L including visible light.

This configuration can reduce the number of components of psychological state display system 1a according to the variation and can simplify the configuration of psychological state display system 1a.

Furthermore, for example, imaging device 200 captures an infrared image that includes blood vessel information indicating vasoconstriction of each of the plurality of persons. Based on the blood vessel information included in the captured infrared image, generation device 300 generates vitals information indicating the vital signs of at least one person among the plurality of persons. Display device 400 displays the generated vitals information.

With this configuration, psychological state display system 1 can not only visualize a change over time in the psychological state of a person but also visualize the vitals information of the person and a change over time in that vitals information.

Furthermore, for example, near-infrared light source 100 and imaging device 200 are installed in an entertainment space, a public space, or a learning space.

Thus, psychological state display system 1 can be implemented that can easily visualize a change in the psychological state of a person even in a space where the presence, the intensity, and the color tone of the visible light easily change to a great extent or a space where a person is irradiated with a plurality of rays of white illumination light of different chromaticity.

Other Embodiments

Thus far, the embodiment has been described, but the present invention is not limited to the embodiment described above.

According to the embodiment and the variation described above, output light L includes the first near-infrared light and the visible light, but this is not a limiting example. Output light L may include only the first near-infrared radiation. Alternatively, output light L may further include an electromagnetic wave other than the first near-infrared radiation or the visible light.

Herein, examples that can be used as such an electromagnetic wave include at least one of an ultraviolet radiation, a mid-infrared radiation, or a far-infrared radiation.

For example, an ultraviolet radiation has a property of being converted into visible light upon interacting with phosphor. Phosphor is included, for example, in bleach contained in clothes. Therefore, when a person wearing such a piece of clothing is irradiated with output light L that includes an ultraviolet radiation, visible light is outputted from that piece of clothing. Therefore, for example, the plurality of persons or the administrator of the psychological state display system can easily recognize that output light L that includes an ultraviolet radiation and a first near-infrared radiation is being outputted.

Furthermore, for example, a mid-infrared radiation and a far-infrared radiation have a relatively high heating effect.

Therefore, when output light L includes a mid-infrared radiation or a far-infrared radiation, this configuration makes it possible to implement a psychological state display system having a heating effect, although slight, in a cold region.

Near-infrared light source 100 controls the first near-infrared radiation, the visible light, and the electromagnetic wave independently of each other, and controls at least one of the on/off or the dimming of each of the first near-infrared radiation, the visible light, and the electromagnetic wave.

As near-infrared light source 100 controls the first near-infrared radiation, the visible light, and the electromagnetic wave in this manner, this control makes it possible to implement psychological state display system 1 that is advantageous in visualizing a psychological state based on the first near-infrared radiation and in freely controlling the stage lighting effects that are based on the visible light and the electromagnetic wave.

Furthermore, the method of communication between the devices described according to the foregoing embodiment is merely one example. There is no particular limitation on the method of communication between the devices.

In the foregoing embodiment, a process executed by a specific processor may be executed by another processor. Furthermore, the order of a plurality of processes may be modified, or a plurality of processes may be executed in parallel.

The constituent elements, such as the generator, according to the foregoing embodiment may each be implemented through the execution of a software program suitable for the corresponding constituent element. The constituent elements may each be implemented as a program executing unit, such as a central processing unit (CPU) or a processor, reads out a software program recorded in a recording medium, such as a hard disk or a semiconductor memory, and executes the software program.

Meanwhile, the constituent elements, such as the generator, may each be implemented by hardware. For example, the constituent elements, such as the generator, may each be a circuit (or an integrated circuit). These circuits may be configured as a single circuit as a whole or may be configured as respectively separate circuits. Furthermore, these circuits may each be a general purpose circuit or a dedicated circuit.

Furthermore, general or specific aspects of the present invention may be implemented in the form of a system, an apparatus, a method, an integrated circuit, a computer program, or a computer readable recording medium, such as a CD-ROM. Furthermore, the general or specific aspects may be implemented through a desired combination of a system, a device, a method, an integrated circuit, a computer program, and a recording medium. For example, the present invention may be implemented in the form of the psychological state display system according to the embodiment described above or may be implemented in the form of a psychological state display method to be executed by the psychological state display system. The present invention may be implemented in the form of a program that causes a computer to execute such a psychological state display method or may be implemented in the form of a non-transitory recording medium having such a program recorded thereon. Such a program includes an application program for causing a computer, such as a general purpose information terminal, to function as the generation device according to the embodiment described above.

Aside from the above, an embodiment obtained by making various modifications that a person skilled in the art can conceive of to the foregoing embodiment or an embodiment achieved by combining, as desired, the constituent elements and the functions in the embodiment within the scope that does not depart from the spirit of the present invention is also encompassed by the present invention.

The invention claimed is:

1. A psychological state display system comprising:

a near-infrared light source that outputs output light toward a plurality of persons, the output light including a first near-infrared radiation having a wavelength of greater than or equal to 780 nm and less than 2,500 nm and an output of greater than or equal to 10 W and smaller than or equal to 3 KW;

an imaging device that receives the first near-infrared radiation included in the output light outputted and captures an infrared image of the plurality of persons;

a generation device that, using a trained machine learning model that receives an input of the infrared image captured and outputs a psychological state of at least one person among the plurality of persons indicated by the infrared image, generates psychological data indicating the psychological state; and a display device that displays a change over time in the psychological data generated.

2. The psychological state display system according to claim 1, wherein the first near-infrared radiation has a peak wavelength in a range of wavelengths greater than or equal to 780 nm and less than 2,500 nm.

3. The psychological state display system according to claim 1, wherein the near-infrared light source includes a first solid-state light emitting element that outputs the first near-infrared radiation.

4. The psychological state display system according to claim 1, wherein the near-infrared light source includes:

a second solid-state light emitting element that outputs excitation light; and a phosphor member that, based on the excitation light outputted, outputs wavelength-converted light as the first near-infrared radiation.

5. The psychological state display system according to claim 1, wherein the output light includes visible light.

6. The psychological state display system according to claim 5, wherein the near-infrared light source:

controls the first near-infrared radiation and the visible light independently of each other; and controls at least one of on/off or dimming of each of the first near-infrared radiation and the visible light.

7. The psychological state display system according to claim 1, wherein a received light signal intensity obtained as the imaging device receives the first near-infrared radiation reflected by the plurality of persons while the output light including the first near-infrared radiation is being outputted is a first received light signal intensity, a second near-infrared radiation different from the first near-infrared radiation is emitted toward the plurality of persons while the output light including the first near-infrared radiation is not being outputted, the second near-infrared radiation is a near-infrared radiation outputted from a light source different from the near-infrared light source, a received light signal intensity obtained as the imaging device receives the second near-infrared radiation reflected by the plurality of persons is a second received light signal intensity, and a minimum value of the first received light signal intensity is greater than a maximum value of the second received light signal intensity.

8. The psychological state display system according to claim 1, wherein the near-infrared light source outputs the output light toward at least one person among the plurality of persons from a direction other than a forward direction that a head of the at least one person faces.

9. The psychological state display system according to claim 8, wherein an area of an irradiation target region to be irradiated with the first near-infrared radiation is greater than or equal to 10 m² and less than 10,000 m².

10. The psychological state display system according to claim 8, wherein a distance between the near-infrared light source and a person, among the plurality of persons, who is located closest to the near-infrared light source is greater than or equal to 50 cm and less than 30 m.

11. The psychological state display system according to claim 8, wherein when the near-infrared light source is viewed in a vertical direction, a divergence angle of the near-infrared radiation in a horizontal direction is greater than or equal to 30° and smaller than or equal to 180°.

12. The psychological state display system according to claim 1, wherein the generation device determines a stimulus to be provided to the plurality of persons, based on the psychological data generated.

13. The psychological state display system according to claim 12, further comprising:

a control device that controls a stimulus device that provides the stimulus to the plurality of persons, wherein the control device controls the stimulus device to provide the stimulus determined to the plurality of persons.

14. The psychological state display system according to claim 13, further comprising:

the stimulus device, wherein the control device controls the stimulus device to provide the stimulus determined to at least one or more of the plurality of persons.

15. The psychological state display system according to claim 13, wherein the stimulus determined is a stimulus that acts on at least one of vision, hearing, smell, and touch of the plurality of persons.

16. The psychological state display system according to claim 13, wherein the control device controls the stimulus device to shut off or reduce the stimulus provided to the plurality of persons.

17. The psychological state display system according to claim 12, wherein when the psychological data generated indicates that the psychological state of one or more persons among the plurality of persons is a predetermined psychological state, the generation device determines a stimulus to be provided to the one or more persons, based on the predetermined psychological state.

18. The psychological state display system according to claim 14, wherein the stimulus device is the near-infrared light source that outputs the output light including visible light.

19. The psychological state display system according to claim 1, wherein the imaging device captures the infrared image that includes blood vessel information regarding vasoconstriction of each of the plurality of persons, based on the blood vessel information included in the infrared image captured, the generation device generates vitals information indicating a vital sign of at least one person among the plurality of persons, and the display device displays the vitals information generated.

20. The psychological state display system according to claim 1, wherein the near-infrared light source and the imaging device are installed in an entertainment space, a public space, or a learning space.

* * * * *